United States Patent [19]
Thompson et al.

[11] Patent Number: 5,695,890
[45] Date of Patent: *Dec. 9, 1997

[54] HETEROLAMELLAR PHOTOELECTROCHEMICAL FILMS AND DEVICES

[75] Inventors: Mark E. Thompson, Anaheim Hills, Calif.; Jonathan Lee Snover, Raleigh, N.C.; Vijay Joshi, Livingston, N.J.; Lori Ann Vermeulen, Hurst, Ill.; Xiaozhang Tang, New Brunswick, N.J.; Elena Suponeva, Los Angeles, Calif.; Houston Byrd, Birmingham, Ala.

[73] Assignee: The Trustees of Princeton University, Princeton, N.J.

[*] Notice: The term of this patent shall not extend beyond the expiration date of Pat. No. 5,500,297.

[21] Appl. No.: 582,021

[22] Filed: Jan. 2, 1996

Related U.S. Application Data

[63] Continuation-in-part of Ser. No. 517,095, Aug. 21, 1995, and Ser. No. 287,140, Aug. 8, 1994, Pat. No. 5,480,629, each is a continuation-in-part of Ser. No.103,968, Aug. 9, 1993, Pat. No. 5,500,297.

[51] Int. Cl.$^6$ ............................................. H01M 6/30
[52] U.S. Cl. ........................................................ 429/111
[58] Field of Search ............................ 429/111; 136/263

[56] References Cited

U.S. PATENT DOCUMENTS 5,500,297  3/1996  Thompson et al. ............... 428/411.1

*Primary Examiner*—Aaron Weisstuch
*Attorney, Agent, or Firm*—Woodbridge & Associates

[57] ABSTRACT

Multi-layered compositions having a plurality of pillared metal complexes disposed on a supporting substrate, the pillars comprising divalent electron acceptor moieties with a phosphonate or arsenate at each end. Each layer of parallel pillars is separated by a layer of a group (IVA), (IVB), (IIIA) or (IIIB) metal or a lanthanide. The compositions can further comprise particles of at least one Group VIII metal at zero valence entrapped within each layer of the complex. The complexes can also incorporate "stalactites" and "stalagmites" of capped arsonato or phosphonato ligands interspersed with the pillars providing a series of interstices about each electron accepting group. The supporting substrate can be comprised of an organic polymer template. The complexes are useful for the conversion and storage of solar energy, for the production of photocurrents, and as catalysts for reduction reactions, for example, the production of hydrogen peroxide from oxygen and hydrogen gases, the production of $H_2$ gas from water, and the reduction of ketones to form alcohols.

4 Claims, 8 Drawing Sheets

HETEROLAMELLAR PHOTOELECTROCHEMICAL FILMS AND DEVICES

This is a continuation-in-part of U.S. patent application Ser. No. 08/517,095, filed on Aug. 21, 1995 and Ser. No. 08/287,140, filed on Aug. 8, 1994, (now U.S. Pat. No. 5,480,629) both of which are continuation-in-part applications of U.S. patent application Ser. No. 08/103,968, filed on Aug. 9, 1993, (now U.S. Pat. No. 5,500,297) the disclosures of which is incorporated herein by reference.

TECHNICAL FIELD

The present invention pertains to stable electron acceptor compositions which have efficient and sustained photoinduced charge separation states and methods of using same.

BACKGROUND OF THE INVENTION

Solar energy can be used and stored by the efficient production of long-lived photo-induced charge separation-a state achieved in photosynthetic systems by the formation of a long-lived radical pair. A number of artificial systems have been reported that efficiently undergo photochemical charge transfer; unfortunately, the thermal back electron transfer often proceeds at an appreciable rate, limiting the utility of these systems. What is needed is a systems which has very efficient photoinduced charge transfer, and forms a charge-separated state which is long lived in air. The charge separation in these systems typically involves a redox reaction between a photo excited donor and a suitable acceptor, resulting in the production of radical ion pairs illustrated by the formula:

$$D+h\nu \rightarrow D^* \quad (1a)$$

$$D^*+A \rightarrow A^-+D^+ \quad (1b)$$

$$D^++A^- \rightarrow D+A \quad (2)$$

The cation and anion generated in this way are better oxidants and reductants, respectively, than either of the neutral ground-state molecules. To harvest the light put into this system, the oxidizing and reducing power of the photogenerated species must be used before the electrons are transferred back (equation 2) generating the starting materials. It is desirable to control this photochemically unproductive thermal fast back electron transfer reaction. One method has been to incorporate the donors and acceptors into solid matrices.

Design and characterization of chemically sensitive interfaces and thin films has focused on attempts to mimic the highly efficient processes observed in biological systems, many of which occur in or at membranes. Thus, a key goal in this area is the fabrication of an artificial system for the conversion of solar energy into chemical or electrical energy. This approach to energy conversion can take a number of forms, ranging from the design of novel photovoltaic devices to the search for an efficient and cost-effective method to photochemically convert liquid water to gaseous hydrogen and oxygen. Properly designed systems can use the photoinduced charge separation to generate a photocurrent.

In a process to generate chemical energy, $D^+$ and A are used to drive uphill chemical reactions, such as the oxidation and reduction of water, respectively. In order to generate electrical energy the same species can be used as the anode and cathode of a photocell. In order for either of these processes to be efficient back electron transfer (equation 2) must be prevented. In order to retard back electron transfer it is important to control both the structural and electronic properties of the system. In natural reaction centers this goal is achieved by fixed geometrical arrangements of electron donors, intermediate carriers and electron acceptors within the membrane. In artificial systems, the electron donors and acceptors with chosen redox potentials may be arranged in a fixed geometry using simple self-assembly techniques.

The individual components in the charge separated state have the appropriate potentials to carry out the reduction and oxidation of water. Unfortunately, these direct reactions are kinetically limited, such that catalysts are required to overcome the kinetic barriers. Colloidal platinum particles are ideal catalysts for the reduction of water to give $H_2$. In systems used for photoreduction of water, the close contact of high potential radicals formed in the compounds and Pt particles is advantageous, because electron transfer from reduced viologen to Pt particles should compete effectively with back electron transfer. These platinum particles may be present in the reaction solution, incorporated into the structure of the compositions, or both.

Compounds which can carry out reduction reactions, using hydrogen gas as their reducing equivalents, are useful as catalysts for the conversion of mixtures of hydrogen and oxygen to hydrogen peroxide. Hydrogen peroxide is a very large volume chemical. The United States annual production is greater than 500 million lbs. Several processes have been patented for the production of hydrogen peroxide, which depend on the two following reactions. The goal is to promote reaction (3) and retard reaction (4):

$$H_2+O_2 \rightarrow H_2O_2 \quad (3)$$

$$H_2O_2+H_2 \rightarrow 2\,H_2O \quad (4)$$

A number of catalysts for this conversion have been reported including both homogeneous and heterogeneous catalysts.

Compositions of the present invention are capable of producing a sustained photoinduced charge separation state which renders the compositions useful in solar energy conversion and storage. Multilayer thin films of the present invention composed of donor and acceptor layers produce photocurrents when irradiated with light. In addition, the compositions permit reduction of various metal ions to produce the zero-valence metal in colloidal form entrapped in the matrices of the compositions. These latter matrices containing the zero-valence metal have a variety of uses such as in the decomposition of water to yield hydrogen gas and the sensing of oxygen. In addition, the zero-valence metal matrices can be used in catalysis, as for example in the production of hydrogen peroxide and the oligomerization of methane to form higher hydrocarbons.

SUMMARY OF THE INVENTION

The present invention provides multi-layered compositions, each layer having a plurality of parallel "pillars" comprising divalent electron acceptor or donor moieties with a phosphonate or arsenate at each end. Each layer of parallel pillars is separated by a layer of a group (IVA), (IVB), (IIIA) or (IIIB) metal or a lanthanide.

The complex can further comprise particles of at least one Group VIII metal at zero valence entrapped within each layer of the complex. The complexes can also incorporate "stalactites" and "stalagmites" of capped arsonato or phosphonato ligands interspersed with the pillars providing a series of interstices about each electron accepting group.

The donor or acceptor moiety of each pillar layer can be selected independently from the other layers. Thereby films can be homogenous, where the donor/acceptor moiety of each layer is the same; or heterogeneous, where the donor/acceptor moiety of one or more adjacent layers can be different.

The complexes are useful for the conversion and storage of solar energy, the production of photocurrents, and as catalysts for reduction reactions, for example, the production of hydrogen peroxide from oxygen and hydrogen gases, the production of $H_2$ gas from water, and the reduction of ketones to form alcohols.

DETAILED DESCRIPTION

Figure 1:
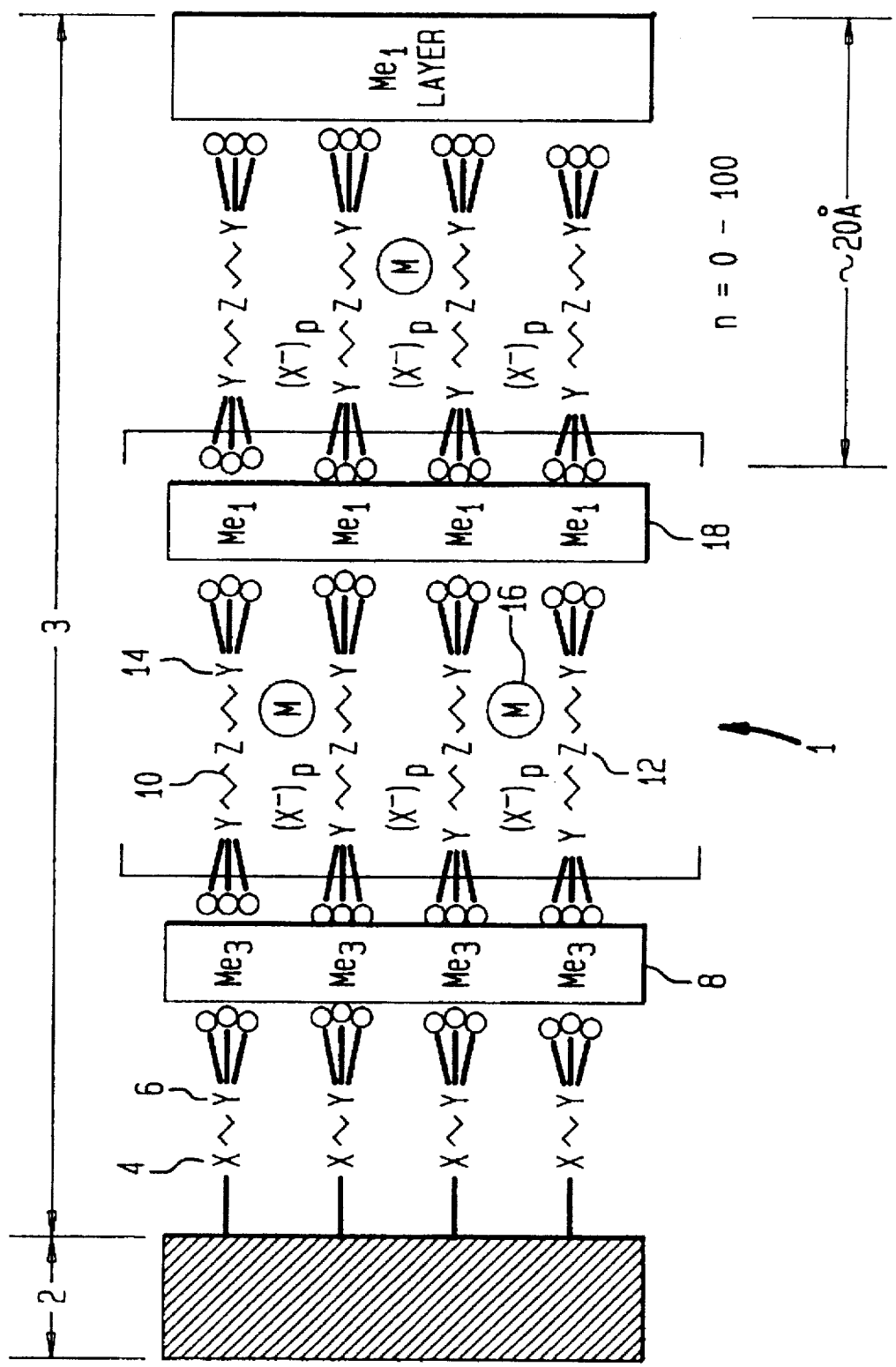
FIG. 1 is a schematic view of the highly ordered structure of a substrate and film according to the present invention.

During the course of this description, like numbers will be used to identify like elements according to the different figures which illustrate the invention.

In general the invention relates to layered compositions comprising two or more adjacent metal layers 68, independently of the other, comprised of atoms of a divalent, trivalent, or tetravalent metal of Group III, IVA, IVB having an atomic number of at least 21 or atoms of a lanthanide, which form a cohesive layer. The metal layers are adjacently spaced and in substantially parallel relation to each other and to the substrate 62. Disposed between, and in substantially perpendicular relation to the metal layers, are organic pillars 66 which are independently, one from the other, covalently joined to two of the adjacent metal layers and thus forming interstices between the pillars and the two adjacent metal layers. This layered composition can take the form of, for example, a thin film or a micro-crystalline solid.

The organic pillars are illustrated by the formula:

$$-(Y^1O_3-Z-Y^2O_3)-$$  L wherein each of $Y^1$ and $Y^2$, independently of the other, is phosphorous or arsenic;

Z is an electron accepting or donating divalent group containing a conjugated network which is capable of alternating between a stable reduced form and a stable oxidized form;

A sufficient number of anions are bound to the metal ions which make up the metal layers, such that the metal ions have an effective valence of from $^+1$ to $^+6$, preferably $^+3$ or $^+4$.

A separate group of anions is present within the lattice formed by the pillars and metal atoms to counterbalance any residual charge in the composition.

Additionally, the composition can comprise particles of at least one Group VIII metal at zero valance trapped in the interstices between the pillars and the adjacent metal layers. These particles may enhance the function of the composition, for example, by acting as a catalyst for reduction reactions. The compositions can also comprise organic ligands disposed between the metal layers and between the pillars which are independently, one from the other, covalently joined to one of the metal layers. The ligands are illustrated by the formula:

$$-Y^3O_3-R^3$$  II.

wherein $Y^3$ is phosphorous or arsenic and $R^3$ is a non-reducible capping group.

In a first embodiment, the invention relates to a composite composition in which a film is disposed on a supporting substrate. In that form, the layer closest to the substrate is bound to the substrate by a linking means. The substrate can be, for example metals, glass, silicas, polymers, semiconductors (e.g., silicon, gallium arsenide), combinations thereof such as a gold layer on an aluminum base, and the like. The substrate can be in any form, for example sheets, foils, plates, films, electrodes, colloidal particles in suspension, polymer templates, high surface area supports, and the like. The surface of the substrate can be uniform (smooth) or non-uniform (rough). The film is composed of a plurality of pillared metal complexes, each of the formula:

$$-L-[(Y^1O_3-Z-Y^2O_3)Me^r]_k\cdot k^*p(X^{q-})$$  III.

in which:

L is a linking means;

each of $Y^1$ and $Y^2$, independently of the other, is phosphorus or arsenic;

Z is a divalent group which reversibly forms a stable reduced form and stable oxidized form;

X is anion;

$Me^y$ is $Me^1_nW_m$, where $Me^1$ is a divalent, trivalent, or tetravalent metal of Group III, IVA, or IVB having an atomic number of at least 21 or a lanthanide;

W is an anion, such as, but not limited to, halides or pseudohalides, or —OH;

n is 1, 2, or 3;

m is 0, 1, 2, 3, or 4;

k has a value of from 1 to about 250;

p has a value of 0, 1, 2, or 3; and q is the charge on the anion, where for each additional k value, another layer is added to the film.

$Me^1$ can be, for example, a group IVA metal having an atomic number of at least 21, such as germanium, tin, or lead, a group IVB metal such as titanium, zirconium, or hafnium, a group IIIA metal having an atomic number of at least 21, such as gallium, indium, or thallium, a group IIIB metal such as scandium, yttrium, or a lanthanide, as for example, lanthanum, cerium, praseodymium, etc. Of these, titanium, zirconium, hafnium, germanium, tin, and lead are preferred with zirconium being particularly useful.

Each of $Y^1$ and $Y^2$ is phosphorus or arsenic, preferably phosphorus, each of $Y^1O_3$ and $Y^2O_3$ thus being a phosphonato or arsenato group.

The group Z is divalent, being bound to the phosphorus or arsenic atom of the phosphonato or arsonato group defined by $Y^1O_3$ and $Y^2O_3$. In practice, the precise structure of the group Z is of lesser importance than its electronic properties; Z must be capable of existing both in a stable reduced form and reversibly in a stable oxidized form.

In one embodiment, Z can contain two conjugated cationic centers which together have a negative $E°_{red}$ value; i.e., a reduction potential below that of hydrogen. The two conjugated cationic centers can be, for example, tetravalent nitrogen atoms which are conjugated ring members in an aromatic ring system. In one embodiment, each tetravalent nitrogen atom is a ring member in a separate aromatic ring system and two such ring systems, which can be of the same or different structure, are joined to one another directly or through a covalent bond. Each such aromatic ring system can be a monocycle such as pyridine, pyrazine, or pyrimidine. Alternatively, each aromatic ring system can be a fused polycycle in which a pyridine, pyrazine, or pyrimidine ring is fused to one or more benzo or naphtho ring system, as for example quinolinium, isoquninolinium, phenanthridine, acridine, benz[h]isoquinoline, and the like.

The two aromatic ring systems, which can be of the same or different structure, alternatively can be linked through a divalent conjugated system as for example diazo (—N=N—), imino (—CH=N—), vinylene, buta-1,3-diene-1,4-diyl, phenylene, biphenylene, and the like.

In a further embodiment, the two conjugated cationic centers can be in a single aromatic system such as phenanthroline, 1,10-diazaanthrene, and phenazine.

Typical dicationic structures suitable as Z thus include 2,2-bipyridinium, 3,3-bipyridinium, 4,4-bipyridinium, 2,2-bipyrazinium, 4,4-biquinolinium, 4,4-biisoquninolinium, 4-[2-(4-pyridinium, 4,4'-bis(4-pyridinium) biphenyl, and 4-[4-(4-pyridinium)phenyl]pyridinium.

The aromatic systems in which the two conjugated cationic centers are located can be unsubstituted or substituted, as for example with alkyl of 1 to 6 carbon atoms or alkoxy of 1 to 6 carbon atoms. Such substitution can be inert or can have an effect on the reduction potentials of the cationic centers sterically or through induction.

While the two cationic centers must be linked through conjugation, the entire system comprised by Z need not be conjugated. Thus Z can be joined to each of $Y^1O_3$ and $Y^2O_3$ through a conjugated or non-conjugated bridge. Hence one highly desirable structure for Z is characterized by the structure:

$$-(R^1)_n-Z'-(R^2)_m-\qquad \text{IV.}$$

in which Z' is a divalent aromatic group containing at least two conjugated tetravalent nitrogen atoms; each of n and m, independently of the other, has a value of 0 or 1; and each of $R^1$ and $R^2$, independently of the other, is a divalent aliphatic or aromatic hydrocarbon group. Typically each of n and m will be 1 and each of $R^1$ and $R^2$, independently of the other, will be a straight or branched divalent alkane chain of six or less carbon atoms, as for example methylene, ethano, trimethylene, propane-1,2-diyl, 2-methylpropan-1, 2-diyl, butane-1,2-diyl, butane-1,3-diyl, tetramethylene, and the like or a divalent aryl, substituted or unsubstituted, as for example benzyl.

Other forms of Z include 1,4-Bis(4-phosphonobutylamino)benzene (PAPD); porphyrin derivatives and phthalocyanin derivatives. Using ringed Z moities would result in pillars illustrated by the formula:

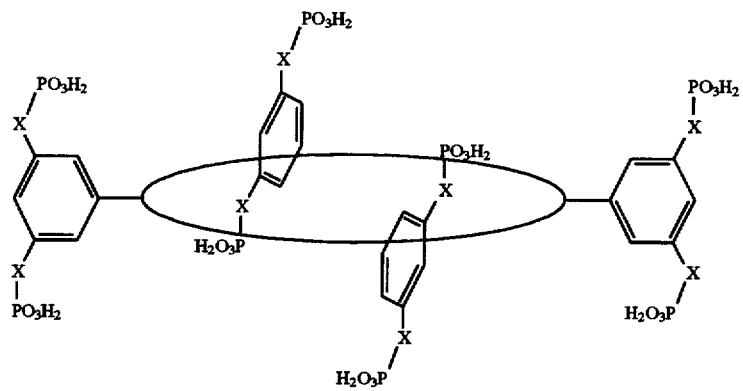

where X is O or $(CH_2)_y$, where y is 1 to 6.

The group X is an anionic group one or more of which (depending on the value of k and the charge of X) will balance the cationic charges of Z. and result in a net positive valence of $Me^y$ being equal to (4-p*q). The precise nature of X is relatively unimportant and X can be for example a halogen anion such as chloride, bromide, iodide, a pseudohalide, sulfate, sulfonate, nitrate, carbonate, carboxylate, etc.

The group W is an anionic group one or more of which (depending on the metal ion, $Me^1$, used) will result in a net positive valence of $Me^y$ being equal to (4-(p*q)). The precise nature of W is relatively unimportant and W can be for example a halide, a pseudohalide, hydroxy, etc.

Figure 13:
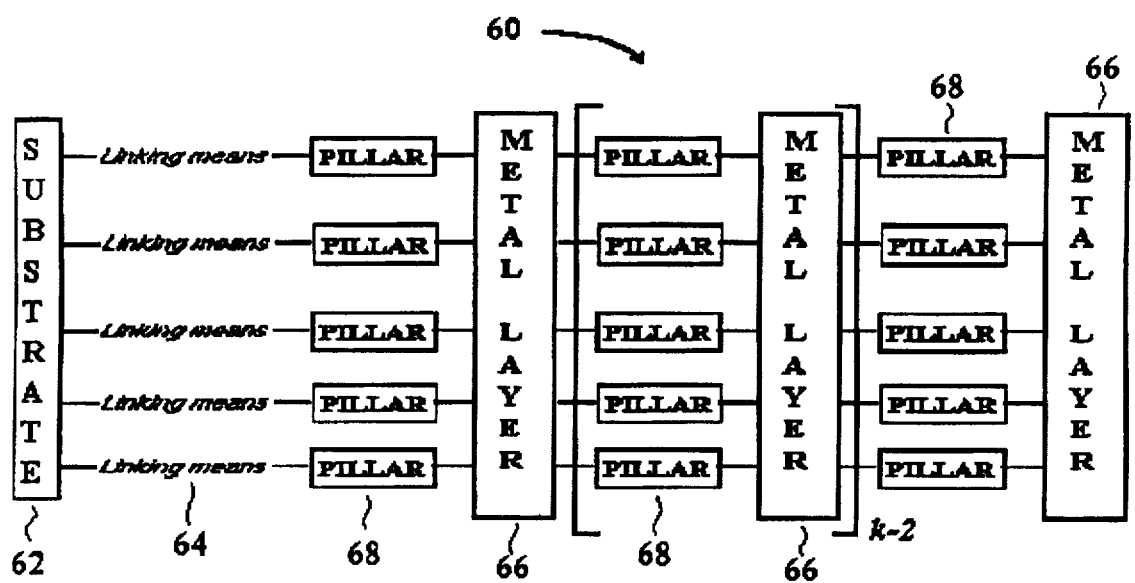
FIG. 13 is a schematic view of the multilayered structure according to the present invention.

Each complex depicted by Formula III is bound to the substrate through the depicted linking means; the plurality of —L—$Y^1O_3$—Z—$Y^2O_3Me^y$ units on the substrate, thereby produces a pillared structure. Each complex can contain one Z-containing unit ("pillar"), in which case k has a value of 1, but preferably k has a value in excess of 1 so that the unit —($Y^1O_3$—Z—$Y^2O_3$)$Me^y$— becomes the monomer of the pillared polymeric complex in which k ranges from 2 to about 250, typically from about 5 to about 100. This multilayered structure is illustrated in FIG. 13.

Such films can be prepared through sequential adsorption reactions analogously to those described by Rong et al., *Coordination Chemistry Reviews*, 97, 237 (1990). The synthetic method and stoichiometry used can effect and determine the resulting configuration and morphology of the compositions.

One preparation method begins with a substrate, which typically is hydroxy terminated, as for example metals (the surfaces of which invariably include the metal oxide), glass, silicas, gallium arsenide, and the like, which is first derivatized with a hydroxy-reactive reagent which introduces the linking means L or components of that linking means. Typically the distal portion of L will terminate in, and thus eventually be bound to $Y^1O_3$ through, a metal atom $Me^3$ which is similar to $Me^1$, i.e., a divalent, trivalent, or tetravalent metal of Group III, IVA, or IVB having an atomic number of at least 21, or a lanthanide.

Thus for example, the substrate can be treated with a compound of the formula:

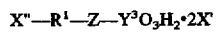    VI.

in which $R^1$ and Z are as herein defined; $Y^3$ is phosphorus or arsenic; X' is an anion analogous to X (X' can be, but need not necessarily be, the same anion as will appear in the final complex) and X" is a reactive halogen such as chloro or bromo. Thereby produced is the intermediate:

    VII.

The foregoing reactions can be conducted in two stages, first by treating the substrate with a compound of the formula X"—$R^1$—Z•2X' and then treating the product with a phosphoryl halide such as phosphoryl chloride or phosphoryl bromide or a corresponding arsonyl halide.

In either aspect of this embodiment, the linking means produced is similar to the repeating unit insofar as it contains —Z—$Y^3O_3$.

Alternatively, the linking means can be dissimilar to the repeating unit. Thus the substrate can be treated with a silane such as an aminoalkyltrialkoxysilane as for example 3-aminopropyltriethoxysilane and this derivatized substrate then treated with a phosphoryl halide such as phosphoryl chloride or phosphoryl bromide or a corresponding arsonyl halide to produce:

[substrate]-alkyl-NH—$Y^3O_3H_2$    VIII.

Other examples of linking means include:

[substrate]-O-alkyl-$Y^3O_3H_2$.    IX.

[substrate]-alkyl-O—$Y^3O_3H_2$    X.

The substrate can also be treated with a thiol to form the linking means. Such thiol linking are particularly useful on gold substrates. Examples of such thiols include thiophosphonic acids having the formula: HS—$(CH_2)_n$—$PO_3H_2$ or thioalkylsilanes having the formula: HS—$(CH_2)_n$—Si(O-alkyl)$_3$, where n is 1 to 16 and alkyl is a straight or branched alkyl of 1 to 16 carbon atoms. Using such thioalkylsilanes results in a linking means intermediate presenting hydroxy groups for the attachment of the metal layer.

Another embodiment uses a template of an organic polymer as a linking means for binding the compositions/films to the surfaces of hydrophobic substrates (e.g., quartz, silicon and metals). These polymer templates are derivatized with phosphonate or arsonate groups, for example, by treating epoxide groups pendant to the polymer backbone with phosphoric acid to yield pendant phosphates.

The hydrophobic polymer template is adsorbed at the surface of the hydrophobic substrate leaving the hydrophilic phosphonate/arsonate groups free for cross-linking. These pendant phosphonate or arsonate groups are cross-linked with ions of the divalent, trivalent, or tetravalent metal of Group III, IVA, IVB having an atomic number of at least 21 or of a lanthanide which form a first metal layer. These polymer templates show good adhesion to the substrate surface, and a yield a highly porous structure (especially on metal substrates).

The polymer can be any polymer having side chains which are capable of being derivatized with phosphonate or arsonate groups. A preferred polymer is polyvinylpyridine in which a fraction, preferably less than one half, of the pyridyl groups have been alkylated with $X(CH_2)_nPO_3H_2$, where X is an anion and where n can be 1 to 16, preferably 2 to 4, (abbreviated PVP—$C_nP$). A polymer backbone which has pendent thiol groups, is preferred for enhanced binding to Au, Ag, and Pt substrates.

In another embodiment, the substrate can be the polymer template itself. Films grown on the polymer template are grown in solution. The hydrophobic properties of the polymer backbone cause the polymer in solution to aggregate into sheet form, with the pendant hydrophillic phosphonate or arsonate groups extending out into the solution, resembling lipid bilayers. This structure can be illustrated by the formula:

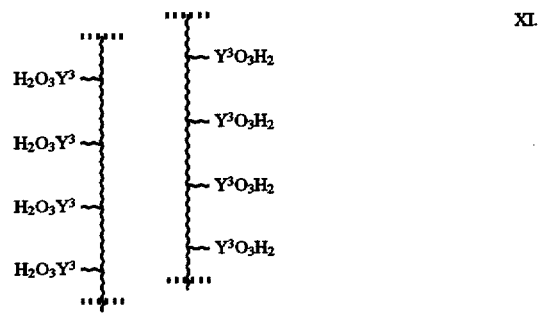    XI.

Colloidal particles of a Group VIII metal, preferably platinum, can be present in the solution. The hydrophobic properties of the aggregate of the polymer backbone attracts the particles. The particles are then trapped within the hydrophobic environment between polymer backbones. This structure can be illustrated by the formula:

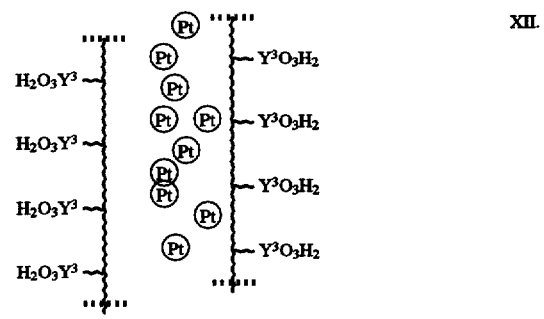    XII.

In either case, the substrate, having a surface rich in phosphonate or arsonate groups then is treated with a reagent providing $Me^3$ ions, e.g., zirconyl chloride. The metal ions bind to, and effectively cross-link, the phosphonate or arsonate groups, in turn producing an intermediate having a metal rich surface and characterized as "substrate-L'—Me³" in which L'—Me³ corresponds to linking means, L, of Formula III, providing a means which (I) on the one hand binds to the substrate and (ii) on the other presents a metal Me³ for further complexing.

Formation of Layers

The substrate-L is then separated from the reagent providing Me³ ions, washed with water, and treated with a solution of a bisphosphonic acid or bisarsonic acid of the formula:

$$H_2Y^1O_3-Z-Y^2O_3H_2 \cdot 2Z' \qquad XIII.$$

in which $Y^1$, $Y^2$, Z, and X' are as defined above. This reaction is complete within a few hours, as for example about 4 to 5 hours, and can be accelerated through the use of moderate heat, as for example from about 80° to about 100° C. The deposition of this layer can be readily monitored spectrophotometrically at wavelengths of from about 260 to about 285 nm. For consistency, generally the range of 280–285 nm is employed. One of the $-Y^1O_3H_2$ and $-Y^2O_3H_2$ groups binds to the metal rich surface, while the other remains uncoordinated, thereby now producing an intermediate having a surface rich in phosphonate or arsonate groups. This intermediate can be depicted as:

$$\text{substrate-L'}-Me^3-Y^1O_3-Z-Y^2O_3H_2 \cdot 2X' \qquad XIV.$$

The substrate-L'—Me³—$Y^1O_3$—Z—$Y^2O_3H_2$·2X' is removed from the solution of the bisphosphonic acid or bisarsonic acid, rinsed thoroughly, and then treated with a reagent providing Me¹ ions to produce a complex of Formula III in which k is 1.

The foregoing sequence of the last two synthetic steps, that is treatment with a bisphosphonic acid or bisarsonic acid followed by treatment with a reagent providing Me¹ ions, is repeated to produce complexes having higher k values. Absorbance, as for example at 280–285 nm, appears to increase linearly with the number of layers and provides a convenient method of monitoring the formation of multilaminar compositions.

The foregoing procedure is readily and preferably modified to entrap atoms of at least one Group VIII metal, as for example platinum, palladium, iron, cobalt, nickel, ruthenium, rhodium, osmium, or iridium, at zero valence within the complexes. Thus following treatment with a bisphosphonic acid or bisarsonic acid but before treatment with a reagent providing Me¹ ions, the sample is immersed in an aqueous solution of a soluble anionic salt of the Group VIII metal. After a short time, the metal anion exchanges with some of the chloride anions in the sample. The stoichiometrics of this exchange will depend upon the respective valences of the two anions. The platinum tetrachloride and platinum hexachloride anions, for example, each have a valence of –2 and if chloride were the starting anion, one anion of either of these metal anions would exchange for two chloride anions.

Following this exchange, treatment with a reagent providing Me¹ ions then is performed as described above. As above, these reactions are repeated until the desired k value is attained. The composite is then simply exposed to hydrogen gas which reduces the metal anion to produce the metal in a zero valence state and colloidal form within the matrix of the composite. As noted previously, such materials are highly effective as catalysts in the production of hydrogen peroxide, the oligomerization of methane to form higher hydrocarbons, the decomposition of water to yield hydrogen gas, and the sensing of oxygen. The compositions also can be utilized to reduce various organic substrates.

When growing the layered compounds on a polymer template as the substrate, the above processes are generally followed, however, the sequential treatment steps are separated by dialysis steps to remove unused reactants, not by rinsing.

It is possible to utilize more than one Group VIII metal in any sample, either using soluble salts of different Group VIII metals in one or more exchanges or conducting one or more exchanges with a first Group VIII metal and subsequent exchanges with a different Group VIII metal. Thus created upon eventual reduction are unique compositions in which colloidal particles of two Group VIII metal having different chemical and electronic properties are entrapped in a single matrix.

One preferred embodiment of these layered compounds, where Z is a viologen, was found to be very efficient at collecting solar radiation and converting that into stored chemical energy. The active wavelengths for this process are in the ultraviolet portion of the spectrum. The energy storage reaction is evidenced by a deep blue color developing in the solid, which persists for long periods of time in the air. This blue color is due to a reduced viologen compound. Reduced viologen reacts rapidly with oxygen when prepared in solution, but is not reactive in the solid became it is trapped inside the dense solid. Oxygen and other external agents are unable to gain access to the reactive interior layers of the solid.

Another preferred embodiment of these layered compounds have a heterolamellar structure. By varying the composition of the pillar layers, primarily by varying Z for each layer, compositions capable of producing a photocurrent are produced. The basic structure is to have one layer of an electron donor composition and a second layer of an electron acceptor composition; the order, i.e., substrate-donor-acceptor or substrate-acceptor-donor, determines the direction of the current flow. One variation on the basic structure is to have several layers of donor (or acceptor) and then several layers of acceptor (or donor), essentially producing thicker donor and acceptor layers. This variation improves photovoltaic properties by increasing the amount of light absorbed. Another variation has repeating, alternating layers of one or more donor layers and one or more acceptor layers (or the opposite order), for example substrate-donor-acceptor-donor-acceptor- etc. (or substrate-acceptor-donor-acceptor-donor- etc.).

In these compositions the electron donor/acceptor property of each layer is relative and not absolute. Thus, a composition could have layers which all are generally considered to have acceptor properties when viewed independently; however, if the layers are formed in, for example, a gradient order of acceptor strength, the first layer would act as a donor in relation to the second layer; the second layer would behave as a donor in relation to the third layer, etc. Compositions using this gradient variation could be illustrated, for example, by the formula:

$$\text{substrate-donor-donor'-donor''-acceptor-acceptor'-acceptor''-etc.}$$

The gradient layers wil hinder back electron transfer and enhance the current flow through, and eventually out of, the fill.

Solid Complexes

In order to make it possible to utilize the stored chemical energy in these compounds, a second embodiment comprises a more open structure. The advantage of the open structures is that they will allow external reagents to have ready access to the photo-generated chemical energy. These solids are composed of a mixture of the pillars of the first embodiment further comprising other smaller ligands interspersed among the pillars. These smaller components leave open space in this new solid. A wide range of different smaller components having different properties and sizes can be used to prepare these solids, leading to a very diverse family of solids. The general formula for the materials of this second embodiment is:

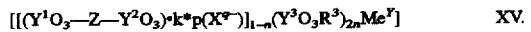   XV.

wherein each of $Y^1$, $Y^2$, Z, X, $Me^Y$, p, and q, are as defined above:

$Y^3$ is phosphorus or arsenic;

n has a value of from 0.1 to 0.8; and $R^3$ is a nonreducible capping group.

In contrast to the materials of the first embodiment which are preferably produced as films on a substrate, the materials of the second embodiment are preferably produced as crystalline or amorphous solids. Analogously to the films of the first embodiment, however, zero valence Group VIII metals can be incorporated in these matrices.

As is apparent from Formula XV, two distinct ligands complex the metals $Me^1$ and $Me^2$. The first of these is analogous to that utilized in Formula III, namely $Y^1O_3$—Z—$Y^2O_3$, and each such ligand is capable of complexing with two metal atoms. The second ligand, $Y^3O_3R^3$, is capable of complexing with only one metal atom. Thus the overall structure may be viewed as a series of parallel layers of the metals $Me^1$ and $Me^2$ with the $Y^1O_3$—Z—$Y_2O_3$ groups serving as pillars. Extending from the metal layers between these pillars are the $Y_3O_3R^3$ groups, forming as it were a series of "stalactites" and "stalagmites" between the pillars. The resultant structure thus has a series of interstices about each —Z— group. The dimensions of these interstices and the hydrophobicity of their defining surfaces can be controlled through selection of $R^3$. Thus one can select relatively small $R^3$ groups such as methyl, creating larger interstices, or relatively larger $R^3$ groups such as phenyl or benzyl, thereby producing relatively smaller interstices. Similarly, one can impart hydrophobic properties to the defining surfaces of the interstices by employing a hydrocarbon group such as propyl for $R^3$ or alternatively decrease the hydrophobicity by employing an $R^3$ group which is substituted with a hydrophilic group such as carboxy. Examples of suitable $R^3$ groups include, but are not limited to: H, $CH_3$, $CH_2Cl$, $CH_2CH_3$, $CH_2CH_2CH_3$, OH, $O^-$, and $OCH_3$.

Because of these interstices, it is possible to introduce Group VIII metals after formation of the complexes, rather than after each step, and then reduce these to zero valence as described above. Hence a complex of Formula XV is treated with an aqueous solution of a soluble anionic salt of a Group VIII metal and the resulting composition treated with hydrogen to produce the Group VIII metal in colloidal form. These compositions can be used as catalysts as previously described.

Moreover, these interstices permit the passage of various molecules into the complexes. For example, oxygen can enter into the matrices and then oxidize the —Z— groups. Since the reduced form of the —Z— group are colored while the oxidized form is white or yellow, this phenomenon can be used to detect oxygen at extremely low levels.

In addition, the ability to control the dimensions of the interstices permits the use of these materials in effecting selective reactions. For example, it is possible to selectively reduce acetophenone in a mixture of acetophenone and 3,5-di-tert. butylacetophenone if the dimensions of the interstices are selected to permit passage of the former molecule but not the latter, more bulky, molecule.

The complexes are readily prepared by treating a mixture of $R^3Y^3O_3H_2$ and $H_2Y^1O_3$—Z—$Y^2O_3H_2$ in the desired molar ratio with a source of metal ions. The reaction can be conducted either by refluxing or hydrothermally and the products are readily isolated and purified.

These porous solids show no photochemical activity in the air due to the ready diffusion of oxygen into the interior of the solid. If the porous solids are irradiated with ultraviolet light under anaerobic conditions the same active species, i.e., reduced electron acceptor, observed for the dense solid is formed. Interestingly, the photochemical efficiency of these open solids is much greater than the dense materials. If the porous solids which were irradiated under anaerobic conditions are treated with air, they are rapidly bleached. Oxygen can freely diffuse into the solids and react with the photo-generated reduced electron acceptor. The product of the reaction between the reduced electron acceptor and oxygen is hydrogen peroxide. One could thus use these materials as catalysts for photochemical production of hydrogen peroxide.

It would be desirable to extract the photochemically stored energy by generating mobile high energy chemical species that could diffuse out of the solid. The goal is to incorporate colloidal metal particles into the preferred viologen containing solids. These metals are well known to act as catalysts for the reaction of reduced viologen with water to produce hydrogen gas. Experiments successfully showed that the materials of the second embodiment could be used to convert solar energy into chemical energy in the form of hydrogen gas. The process involved: 1) photo-generation of reduced viologen, 2) electron transfer from reduced viologen to the colloidal metal particle, 3) protonation of the metal particle and 4) elimination of hydrogen gas. Being a true catalyst these materials will accelerate both forward and reverse reactions equally, thus if of "metallized" material is treated with hydrogen some amount of reduced viologen is generated. On this basis these materials can be used as reducing agents. Photochemical energy is not needed to produce reduced viologen: hydrogen can be used to achieve the same result. The process for this chemical generation of reduced viologen is thus: 1) addition of hydrogen to the metal particle, 2) electron transfer from the metal particle to the viologen molecule forming reduced viologen, and 3) deprotonation of the metal colloid. Experiments have shown that the viologen molecules of these materials can be quantitatively reduced with hydrogen gas at atmospheric pressure.

Figure 2:
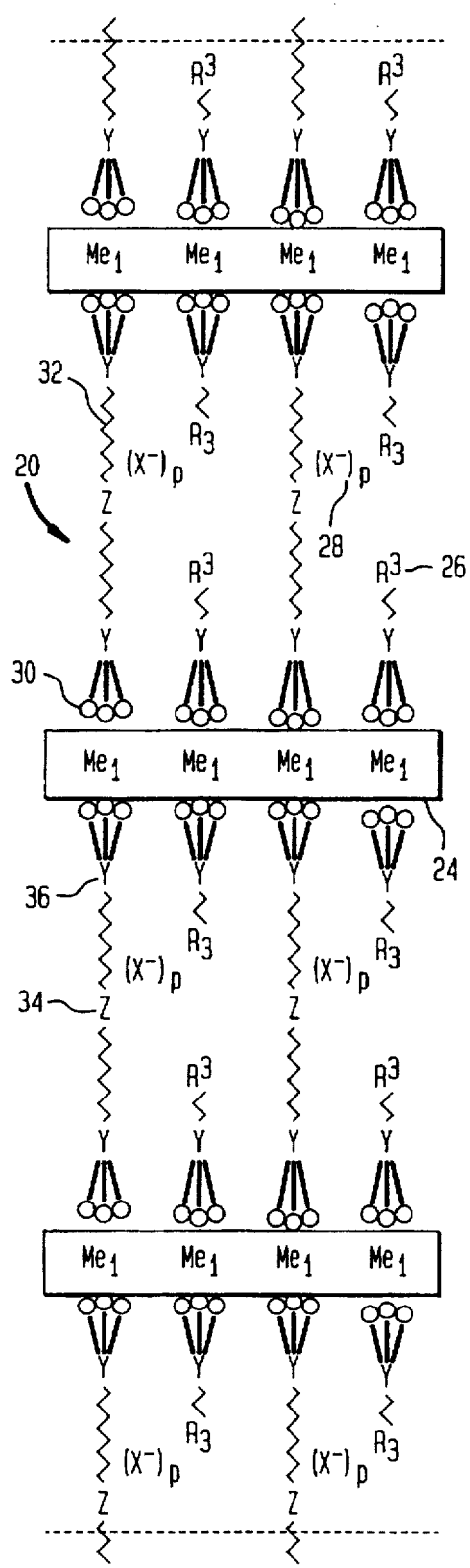
FIG. 2 is a schematic view of a solid composition incorporating "stalactite" and "stalagmite" ligands according to the present invention.
Figure 3:
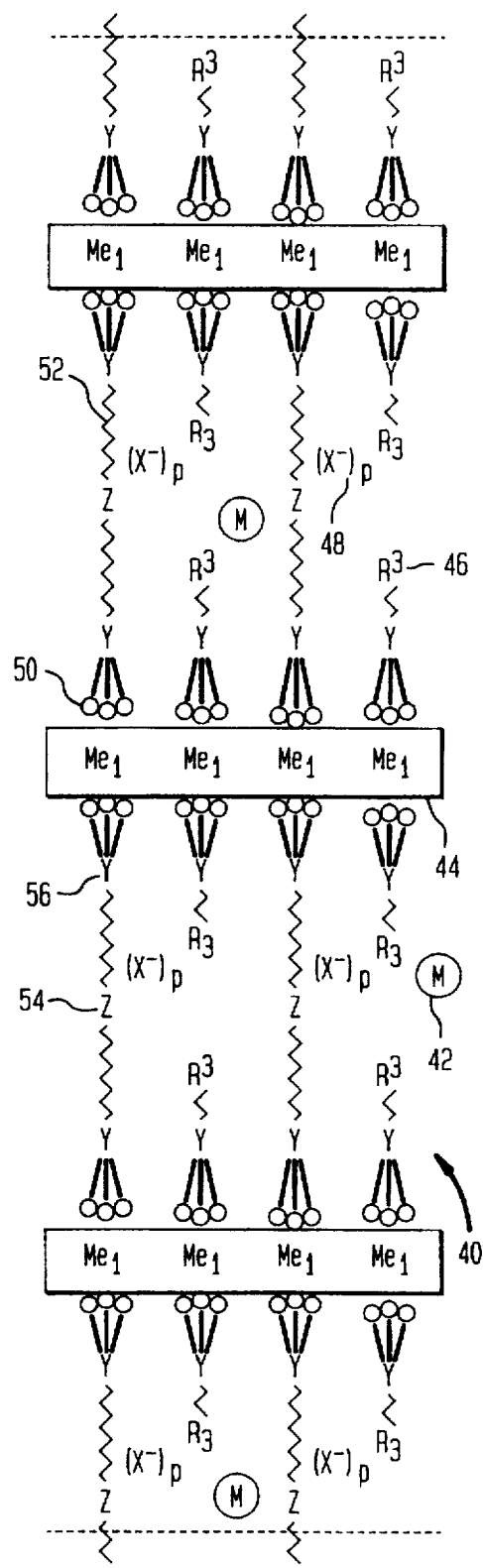
FIG. 3. is a schematic view of a solid of the present invention incorporating metal particles and "stalactite" and "stalagmite" ligands according to the present invention.
Figure 4:
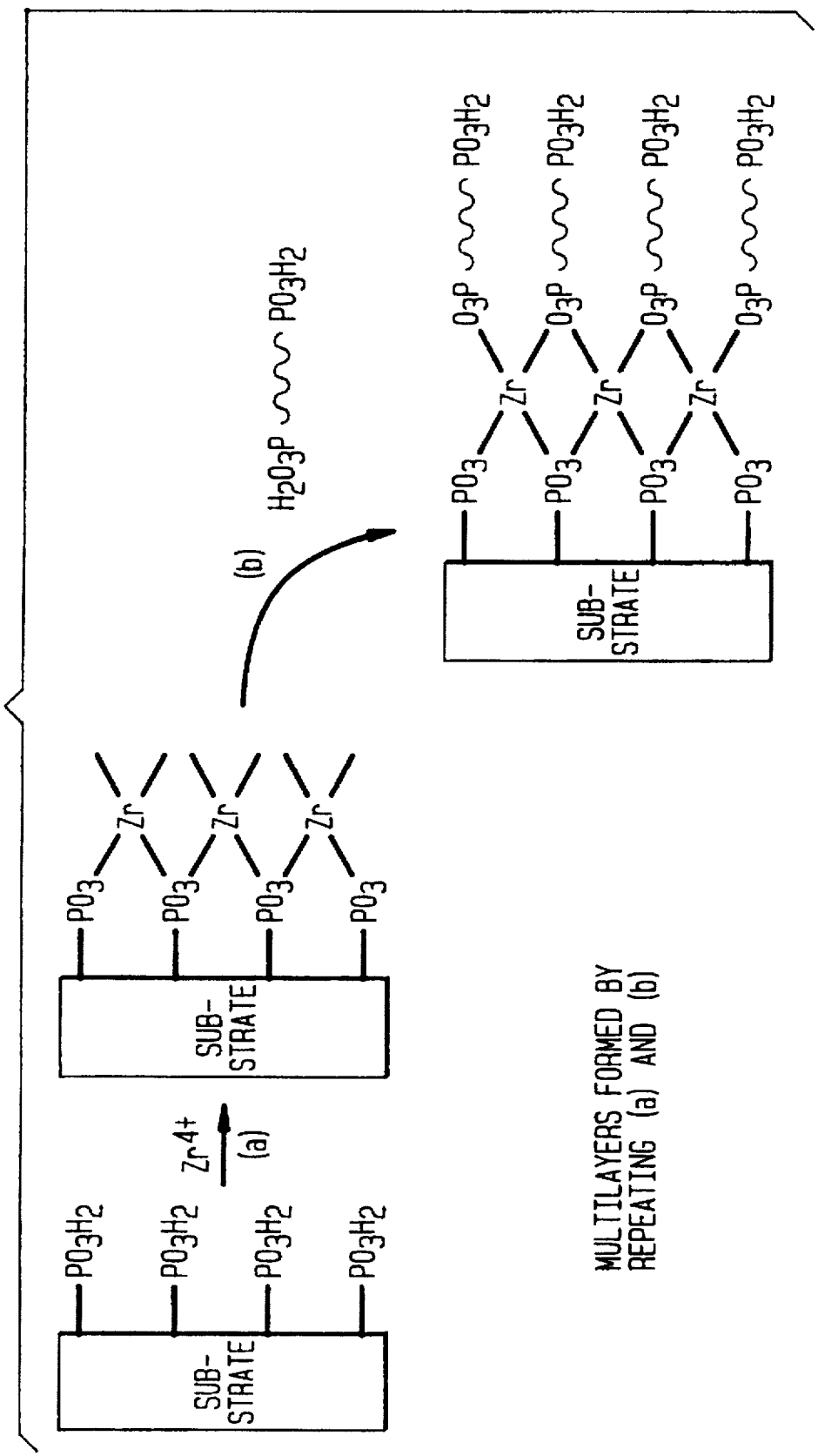
FIG. 4. is a schematic for the production of multilayered films.

Schematic drawings of these porous solids are shown in FIGS. 2 and 3.

The following examples will serve to further typify the nature of the invention but should not be construed as a limitation on the scope thereof which is defined solely by the appended claims.

EXAMPLE 1

Diethyl 2-bromoethylphosphonate (25 g) and 4,4' bipyridine (7.35 g) in 125 mLs of water are refluxed for three days. An equal volume of concentrated hydrochloric acid is added and reflux continued for several hours. The solution is concentrated to 120 mLs by atmospheric distillation and 550 mL of isopropanol are added dropwise with stirring while chilling the mixture in an ice bath. The solid which forms is collected by vacuum filtration and washed with cold isopropanol to yield 1,1'-bisphosphonoethyl-4,4'-bipyridinium dichloride. ($^1$H NMR ($D_2O$) 9.1(d), 8.5(d), 4.2(m), 2.0(m)

ppm; $^{13}C$ NMR($D_2O$) 151, 147, 128, 58, 30 ppm; $^{31}P$ NMR($D_2O$) 17.8 (s) ppm; IR (KBr) 3112, 3014, 1640, 1555, 1506, 1443, 1358, 1281, 1175, 1112, 1020, 936, 816, 485 $cm^{-1}$.)

In a similar fashion, utilizing 2,2-bipyridinium, 3,3-bipyridinium, 2,2-bipyrazinium, 4,4-biquinolinium, 4,4-biisoquninolinium, 4-[2-(4-pyridinium)vinyl]pyridinium, and 4-[4-(4-pyridinium)phenyl]pyridinium, there are respectively obtained 1,1'-bisphosphonoethyl-2,2-bipyridinium dichloride, 1,1'-bisphosphonoethyl-3,3-bipyridinium dichloride, 1,1'-bisphosphonoethyl-2,2-bipyrazinium dichloride, 1,1'-bisphosphonoethyl-4,4-biquinolinium dichloride, 1,1'-bisphosphonoethyl-4,4-biisoquninolinium dichloride, 1-phosphonoethyl-4-[2-(1-phosphonoethyl-4-pyridinium)vinyl]pyridinium dichloride, and 1-phosphonoethyl-4-[4-(1-phosphonoethyl-4-pyridinium)phenyl]pyridinium dichloride.

Other cationic species, such as the corresponding dibromides or disulfates are obtained by substituting the corresponding acids, such as concentrated hydrobromic acid or sulfuric acid, for hydrochloric acid in the procedure of this example.

EXAMPLE 2

Planar substrates of fused silica (9×25 mm) are cleaned in a 1:3 solution of 30% hydrogen peroxide and conc. sulfuric acid, dried at 200° C. for one hour, and then treated with a refluxing solution of 2% (v/v) 3-aminopropyltriethoxysilane in 50 mL of octane for 20 minutes.

The substrates are rinsed with octane and acetonitrile and treated for 12 hours at room temperature with a solution of 10 mM each of phosphoryl chloride and 2,6-lutidine in acetonitrile. After rinsing in water, the substrates are treated with a 65 mM solution of zirconyl chloride for three hours at room temperature.

The foregoing procedure can be used to prepare multilayer films on other substrates such as silicon wafers and vapor deposited gold films.

The substrate next is subjected sequentially to the following two steps.

A). After removal of the solution of zirconyl chloride, the samples are thoroughly rinsed with deionized water and treated with 6 mM of 1,1'-bisphosphonoethyl-4,4'-bipyridinium dichloride at 80° C. for 4 hours and then thoroughly rinsed with deionized water. (Absorption is measured at 284 nm after treatment, the measured extinction coefficient for 4,4'-bipyridinium bisphosphonate being 24,000 $M^{-1}$ $cm^{-1}$ at 265 nm.)

B). The samples next are treated with a 65 mM zirconyl chloride solution at room temperature for one hour and again thoroughly rinsed with deionized water.

Upon completion of one cycle of steps A and B, a plurality of a metal complex of Formula III in which k is 1 is obtained on the planar silica supporting substrate. Each repetition of steps A and B increases the value of k by one. The number of layers, and thus the number of cycles, correlates to absorbance at 284 nm, as can be seen from the following:

| No. of Layers | Absorbance |
| --- | --- |
| 0 | 0.057 |
| 1 | 0.083 |
| 2 | 0.091 |
| 3 | 0.109 |

-continued

| No. of Layers | Absorbance |
| --- | --- |
| 4 | 0.130 |
| 5 | 0.152 |
| 6 | 0.177 |
| 7 | 0.201 |
| 8 | 0.217 |
| 9 | 0.242 |
| 10 | 0.263 |
| 11 | 0.281 |
| 12 | 0.299 |
| 13 | 0.327 |
| 14 | 0.341 |
| 15 | 0.357 |
| 16 | 0.367 |
| 17 | 0.373 |
| 18 | 0.383 |
| 19 | 0.407 |
| 20 | 0.423 |
| 21 | 0.452 |
| 22 | 0.458 |

EXAMPLE 3

By substituting 1,1'-bisphosphonoethyl-4,4'-bipyridinium dibromide in the procedure of Example 2, a series of multilaminar compositions are obtained having the following absorbances:

| No. of Layers | Absorbance |
| --- | --- |
| 1 | 0.083 |
| 2 | 0.098 |
| 3 | 0.113 |
| 4 | 0.157 |
| 5 | 0.182 |
| 6 | 0.239 |
| 7 | 0.286 |
| 8 | 0.350 |
| 9 | 0.353 |
| 10 | 0.391 |
| 11 | 0.465 |
| 12 | 0.557 |

EXAMPLE 4

High quality films also are obtained by employing other metals in place of zirconium in step B, e.g., hafnium, titanium, tin, gallium, etc, as shown in the following procedure.

Planar fused silica substrates (9×25 mm) are cleaned as described in Example 2 and a layer of 3-aminopropyltriethoxysilane is deposited thereon from the gas phase using the method of Haller, *J. Am. Chem. Soc.*, 100, 8050 (1978). The substrates are phosphorylated as described in Example 2, rinsed, and treated with 10 mL of a 65 mM aqueous solution of hafnyl chloride for three hours at room temperature.

Alternating treatments with (A) an aqueous solution containing 6 mM 1,1'-bisphosphonoethyl-4,4'-bipyridinium dibromide and 20 mM sodium chloride at 80° C. for 4 hours and (B) a 65 mM aqueous solution hafnyl chloride at room temperature for 1 hour, with thorough rinsing with deionized water after each, then produce a series of multi-laminar compositions which can be characterized spectrophotometrically at 284 nm.

| No. of Layers | Absorbance |
|---|---|
| 1 | 0.052 |
| 2 | 0.086 |
| 4 | 0.175 |
| 6 | 0.250 |
| 8 | 0.304 |
| 10 | 0.384 |
| 12 | 0.518 |

EXAMPLE 5

The procedure of Example 2 is modified after one or more executions of step A but before execution of the corresponding step B by immersing the samples in a 6 mM aqueous solution of dipotassium platinum tetrachloride for 0.5 hour thereby exchanging one platinum tetrachloride anion for two chloride anions. Step B then is performed as described in Example 2.

After completing the final cycle of steps A and B, the composite is suspended in water and hydrogen gas is bubbled through the mixture for two hours. The platinum is reduced to a zero valence colloidal state entrapped in the overall matrix.

EXAMPLE 6

Silica particles (1 g) are heated in a drying oven for one hour and then stirred with 150 mL of an aqueous solution (60 mM) of zirconyl chloride with the silica (1 g) at 60° C. for two days. The solid is isolated by filtration or centrifugation, washed three times with 150 mL of deionized water, and treated with 150 mL of a 20 mM solution of the 1,1'-bisphosphonoethyl-4,4'-bipyridinium for six hours at 65° C. with agitation. The solid is separated from the aqueous solution and washed three times with deionized water.

The solid then is treated with 150 mL of a 20 mM solution of potassium platinum hexachloride for three hours at room temperature, thereby exchanging one platinum hexachloride anion for two chloride anions.

One hundred and fifty milliliters of a 60 mM solution of zirconyl chloride are added to the solid and the slurry agitated for three hours at room temperature and washed three times with deionized water.

The foregoing steps are repeated four times to produce a pentalaminar composition containing platinum cations. Treatment of an aqueous slurry of the platinized materials with hydrogen then converts the platinum ions into colloidal zero valence platinum metal.

EXAMPLE 7

Zirconyl chloride octahydrate (1.4444 g, 4.8 mmol.) is dissolved in 50 mLs water and 50% hydrofluoric acid (0.756 g, 19 mmol) are added. To this is added a solution of 1 g of 1,1'-bisphosphonoethyl-4,4'-bipyridinium dichloride (2.2 mmol) and 0.516 g of 85% phosphoric acid (4.5 mmol.) in 50 mLs of water. The reaction is refluxed for seven days and the white crystalline product is filtered and washed with water, methanol, and acetone and air-dried to yield the mixed complex:

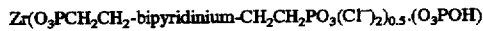

X-Ray diffraction analysis shows d=14 Å. Infra red analysis is as follows: (IR (cm−1), 3126, 3056, 1633, 1562, 1499, 1450, 1217, 1055, 816, 738, 647, 612, 520, 471). $^{31}$P NMR (ppm) are: 3.0, −18.6, −24.5.

EXAMPLE 8

Zirconyl chloride octahydrate (0.21 g, 0.7 mmol.) is dissolved in 10 mLs water and 50% hydrofluoric acid (0.11 g, 2.8 mmol) are added. To this is added a solution of 0.15 g of 1,1'-bisphosphonoethyl-4,4'-bipyridinium dichloride (0.35 mmol) and 0.0686 g of 85% phosphoric acid (0.6 mmol.) in 10 mLs of water. The solution is placed in a 45 mL teflon bomb and the total volume adjusted to 27 mLs. The bomb is sealed and heated at 150° C. for six days to yield the mixed complex:

X-Ray diffraction analysis shows d=14 Å. Infra red and $^{31}$P NMR (ppm) are identical to those given in Example 7.

EXAMPLE 9

Zirconyl chloride octahydrate (0.36 g, 1.12 mmol.) is dissolved in 10 mLs water and 50% hydrofluoric acid (0.179 g, 4.5 mmol) are added. To this is added a solution of 0.25 g of 1,1'-bisphosphonoethyl-4,4'-bipyridinium dichloride (0.56 mmol) and 0.129 g of 85% phosphoric acid (0.11 mmol.) in 50 mLs of 3N hydrochloric acid. The reaction is refluxed for seven days and the white crystalline product is filtered and washed with water, methanol, and acetone and air-dried to yield the mixed complex:

X-Ray diffraction analysis shows d=18.5 Å. Infra red and $^{31}$P NMR (ppm) are identical to those given in Example 7.

EXAMPLE 10

Zirconyl chloride (octahydrate) (0.361 g, 1.12 mmol.) is dissolved in 10 mLs water and 0.189 g of 50% hydrofluoric acid (4.8 mmol.) is added. 1,1'-Bisphosphonoethyl-bipyridinium dichloride (0.25 g, 0.56 mmol.) and phosphorous acid (0.092 g, 1.12 mmol.) are dissolved in 10 mLs of water and this solution is added to the aqueous zirconium solution. The reaction is refluxed for seven days and the white crystalline product is filtered, washed with water, methanol, and acetone and air-dried to yield the mixed complex:

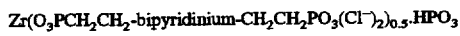

X-Ray diffraction analysis shows d=18.4 Å. Infra red analysis is as follows: 3126, 3056, 2436, 2358, 2330, 1633, 1555, 1499, 1443, 1386, 1210, 1161, 1048, 830, 731, 548. $^{31}$P NMR (ppm) are: 5.5, −9.5.

EXAMPLE 11

By following the procedure of Example 10 but utilizing 0.167 (0.38 mmol.) of 1,1'-bisphosphonoethyl-bipyridinium dichloride and 0.123 g (1.5 mmol.) of phosphorous acid, there is obtained the mixed complex:

The material is amorphous. Infra red and $^{31}$P NMR (ppm) are identical to those given in Example 10.

EXAMPLE 12

By following the procedure of Example 10 but utilizing 0.125 (0.28 mmol.) of 1,1'-bisphosphonoethyl-bipyridinium dichloride and 0.138 g (1.68 mmol.) of phosphorous acid, there is obtained the mixed complex:

The material is amorphous. Infra red and $^{31}$P NMR (ppm) are identical to those given in Example 10.

EXAMPLE 13

Zirconyl chloride (octahydrate) (0.151 g, 0.47 mmol.) is dissolved in 10 mLs water and 50% hydrofluoric acid (0.079 g, 1.9 mmol.) is added. 1,1'-bisphosphonoethyl-bipyridinium dichloride (0.105 g, 0.24 mmol.) and methyl phosphonic acid (0.045 g, 0.47 mmol.) are dissolved in 10 mLs of water and this solution is added to the aqueous zirconium solution. The reaction is refluxed for seven days and the white crystalline product is filtered, washed with water, methanol, and acetone, and air-dried to yield the mixed complex:

The material is amorphous. Infra red analysis is as follows: (IR (cm−1), 3450, 3133, 3056, 2922, 1633, 1555, 1499, 1450, 1309, 1168, 1027, 823, 781, 527).

EXAMPLE 14

In a similar fashion to that described in Example 8, 0.93 mmol. of zirconyl chloride, 0.34 mmol. of 1,1'-bisphosphonoethyl-bipyridinium dichloride, and 0.90 mmoles of 3-aminoethylphosphonic acid are heated in a bomb at 150° C. Upon isolation as therein described the amorphous mixed complex exhibits the following IR spectra: (IR (cm−1), 3500, 3126, 3055, 1646, 1548, 1499, 1443, 1379, 1154, 1041, 865, 823, 760, 731, 541, 499.

EXAMPLE 15

In a similar fashion to that described in either Example 7 or Example 8, zirconyl chloride, 1,1'-bisphosphonoethyl-bipyridinium dichloride, and a phosphorus-containing co-ligand as shown in the following table are allowed to react.

TABLE 1

| Co-ligand | | BPBP* | ZrOCl$_2$ | |
|---|---|---|---|---|
| Reagent | mmols. | (mmols.) | (mmols.) | Conditions |
| CH$_3$PO(OH)$_2$ | 0.47 | 0.23 | 0.47 | Ex. 8: 150° C. |
| CH$_3$CH$_2$PO(OH)$_2$ | 1.12 | 0.56 | 1.12 | Ex. 7 |
| CH$_3$CH$_2$CH$_2$PO(OH)$_2$ | 0.94 | 0.47 | 0.94 | Ex. 8: 200° C. |
| CH$_3$CH$_2$CH$_2$PO(OH)$_2$ | 0.83 | 0.41 | 0.80 | Ex. 8: 140° C. |
| HOCOCH$_2$CH$_2$PO(OH)$_2$ | 0.30 | 0.19 | 0.15 | Ex. 8: 110° C. |
| PhenylPO(OH)$_2$ | 1.12 | 0.56 | 1.12 | Ex. 7 |
| ClCH$_2$PO(OCH$_2$CH$_3$)$_2$ | 1.12 | 0.56 | 1.12 | Ex. 7 |
| BenzylPO(OCH$_2$CH$_3$)$_2$ | 0.70 | 0.33 | 0.65 | Ex. 7 |

*BPBP = 1,1'-bisphosphonoethyl-bipyridinium dichloride
Thereby produced are mixed complexes of the formula:

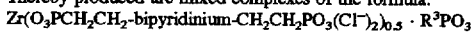

Data on these products are as follows:

TABLE 2

| R$^3$ | X-ray | IR Data |
|---|---|---|
| —CH$_3$ | * | See Ex. 13 |
| —CH$_2$CH$_3$ | d = 10.9Å* | Spectra I |
| —CH$_2$CH$_2$CH$_3$ | d = 11.8Å* | Spectra II |
| —CH$_2$CH$_2$CH$_3$ | d = 13.6Å* | Spectra II |
| —CH$_2$CH$_2$COOH | d = 15.4Å | Spectra III |
| -phenyl | d = 19.7Å* | Spectra IV |
| —CH$_2$Cl | d = 11Å* | Spectra V |
| -benzyl | d = 14.5Å | Spectra VI |

* = Peaks present which are attributable to pure metal bisphosphonate.

Spectra I: (IR(cm−1), 3507, 3126, 3056, 2978, 2943, 2887, 1640, 1563, 1506, 1450, 1393, 1281, 1168, 1048, 872, 830, 738, 541.

Spectra II: (IR (cm−1), 3500, 3126, 3049, 2950, 2866, 1633, 1555, 1499, 1450, 1393, 1246, 1041, 872, 823, 795, 731, 541.

Spectra III: (IR (cm−1), 3500, 2915, 1717, 1633, 1415, 1260, 1027, 816, 752, 534.

Spectra IV: (IR (cm−1), 3500, 3126, 3049, 1633, 1555, 1499, 1443, 1386, 1161, 1055, 865,823, 749, 731, 710, 541.

Spectra V: (IR (cm−1), 3500, 3119, 3049, 1633, 1555, 1499, 1443, 1386, 1161, 1055, 865, 823,759, 731, 710, 541.

Spectra VI: (IR (cm−1), 3500, 3126, 3056, 1633, 1598, 1492, 1450, 1386, 1253, 1161, 1034, 830, 781,738, 696, 626, 541, 499.

EXAMPLE 16

Zr(O$_3$PCH$_2$CH$_2$-bipyridinium-CH$_2$CH$_2$PO$_3$(Cl$^-$)$_2$)$_{0.5}$ (O$_3$POH) The complex prepared as in Example 7 (0.05 g) is stirred with 10 mLs of a 10 mM aqueous solution of dipotassium platinum tetrachloride at room temperature for two days. Over the course of the reaction, the solid changes from white to yellow. The solid then is isolated by filtration, washed extensively with deionized water, and air dried. The solid is suspended in deionized water and hydrogen gas bubbled through the mixture for ten hours. The solid changes from yellow to dark purple. The solid is isolated by filtration, washed with deionized water, and air dried to give a brown solid.

EXAMPLE 17

A substrate of gold deposited on a chromium metal film in turn deposited on glass is treated first with 3-aminopropyltriethoxysilane and then phosphoryl chloride as previously described and then subjected to the procedure of Example 2 three times to prepare a composition of Formula III in which k is 3.

This composition shows a reversible reduction wave at −0.74 V versus a saturated calomel electrode. In water, it shows an irreversible reduction below −1.4 V versus the same standard electrode.

EXAMPLE 18

Twenty-five milligrams of a composition prepared as set forth in Example 6 in 5 mL of 0.1M disodium ethylenediaminetetraacetic acid as a sacrificial reductant in 1 cm$^2$ cell is irradiated with a 200 Watt Hg/Xe lamp. Levels of hydrogen are measured by gas chromatography. The rate of hydrogen production over 18 hours of photolysis is 0.07 mL/hr. Passing the light through a 330 nm cutoff filter (G>330 nm) decreases the rate of hydrogen production by more than an order of magnitude. If the filter is removed the sample photogenerates hydrogen as before. The quantum yield for hydrogen formation (2×moles of $H_2$/moles of photons incident with G<330 nm) in this system is 0.008.

One preferred class of compositions of the second embodiment consists of colloidal particles of Pt and Pd in a porous viologen metal phosphonate matrix. These materials are very different from other Pt+Pd catalysts; the viologen groups make a significant difference in the chemistry involved. The oxygen reduction is carried out by reduced viologen, and not (as is the case in the materials of the DuPont patent) at the colloid surface, since the rate of reduction of oxygen by reduced viologen is much greater than by the colloidal metal particles. By the nature of the way that the solids are prepared, chloride or bromide "promoters" are unavoidably incorporated. A wide range of different materials were tested. A highly active compound contains a mixture of bisphosphonic acid and phosphate (i.e. $Me(O_3P-OH)_1(O_3P-Z-PO_3)_{0.5} \cdot nH_2O \cdot Pt/Pd$). Compounds with the phosphate co-ligand where $R^3$ is OH were found to be between 10 and 100 times more active than compounds where $R^3$ was H, $CH_3$, $CH_2Cl$, $CH_2CH_3$, or $CH_2CH_2CH_3$. A wide range of different ratios of Pd:Pt were also tested. The catalysts have been examined to determine their uniformity and composition. Samples were dissolved in HF and the resulting solutions analyzed by ICP to get the total metal compositions (% by weight of Zr, Pt and Pd, see Table 3). Single particles were analyzed by electron microprobe and found them to have a uniform Zr:Pt:Pd ratio throughout the particles.

A wide range of different electron accepting groups can be associated into this structure that would be amenable to reduction by hydrogen (via colloidal metal particles) and subsequent use as a catalyst for formation of hydrogen peroxide and other reduced species.

The following are results of side-by-side comparisons of the novel catalysts of this invention with other Pt+Pd catalysts which were conducted under identical conditions. (See Table 3). The amount of noble metal (Pt+Pd) in both the materials of this invention and the other materials were analyzed, and then those analyses were used to scale the amount of catalyst in the experiments to have the same amount of noble metal in each case. The comparisons were performed with mixtures of hydrogen and oxygen at atmospheric pressure. At increased pressures the concentration of hydrogen peroxide at steady state (rates of equations 1 and 2 above are identical so that the concentration of $H_2O_2$ is constant over time) will increase.

TABLE 3

|  | Compound of Ex. 24 (below)† | Other Catalyst‡ |
|---|---|---|
| wt % Pt [i.e., Pt/(Pt + Pd)] | 0.1 | 0.05–0.16 |
| [$H_2O_2$] at steady state (M) (at atmospheric pressure) | 0.14* | 0.07 |
| Initial turnover # ($hr^{-1}$) | 30 |  |

*Actually 0.22 M: In this procedure the solution is brought back up to 10 mL before an aliquot is taken, to compensate for evaporation. The steady state concentration of peroxide (rate of reaction 1 = rate of reaction 2) should be constant, regardless of the volume of the sample. Thus when the sample is diluted the amount of peroxide measured is lower. If the conditions of the reaction are the same, giving 0.14 M peroxide, but the reaction mixture is not brought to 10 ml before removing the aliquot the measured concentration is 0.22 M. Thus the steady state concentration of peroxide was underestimated by roughly 50%.
†$Zr(O_3POH)(O_3PCH_2CH_2bipyridiniumCH_2CH_2PO_3)Cl \cdot Pt \cdot Pd$-093
‡The best catalyst disclosed in the DuPont patent (U.S. Pat. No. 4,832,938

A number of different materials according to the present invention, both porous bulk solids and thin films grown on high surface area supports, were prepared and studied.

The bulk solids are prepared by first preparing the layered porous solid of Formula XV; then the halide ions are ion exchanged for polyhalometal anions (such as $PtCl_4^{2-}$); and, then the polyhalometal ions are reduced with hydrogen to give a porous solid with impregnated metal particles.

In carrying out the ion exchange reaction it was found that elevated temperatures are needed. At room temperature $PtCl_4^{2-}$ is taken up preferentially over $PdCl_4^{2-}$, leading to a solid that is richer in Pt than the solution it was prepared from. If the ion exchange is carried out at elevated temperatures the exchange is uniform and the composition in the solid matches that of the solution exactly.

$Zr(O_3POH)(O_3PCH_2CH_2bipyridiniumCH_2CH_2PO_3)Cl$ for the following examples was prepared as in Examples 7, 8, and 9 above. Various ratios of platinum and palladium were then incorporated as follows:

EXAMPLE 19

$Zr(O_3POH)(O_3PCH_2CH_2bipyridiniumCH_2CH_2PO_3)$ Cl.Pt.Pd-58:

170 mg of $Zr(O_3POH)(O_3PCH_2CH_2bipyridinium CH_2CH_2PO_3)Cl$ was mixed with 4.6 ml of $PdCl_2(7.3 \times 10^{-3}M)$ and 2.8 ml of $K_2PtCl_4(6.1 \times 10^{-3}M)$. This mixture was heated to 60° C. with constant stirring for 1 hr. The yellow powder was filtered and washed three to four times with water. The yellow solid was suspended in water and hydrogen gas was bubbled for ½ hr at 60° C. The gray/black solid was filtered and washed first with water and then with ethanol. This solid was then air dried. 0.0072 g of the above solid was dissolved in conc. HCl, a few drops of conc. $HNO_3$, and a few drops of 59% HF. the solution was diluted to 100 ml. and analyzed for Zr, Pt, and Pd by ICP. The analysis (ppm) of the solution are Zr=14.05; Pt=1.01; Pd=0.73

EXAMPLE 20

$Zr(O_3POH)(O_3PCH_2CH_2bipyridiniumCH_2CH_2PO_3)$ Cl.Pt.Pd-32:

260 mg of $Zr(O_3POH)(O_3PCH_2CH_2bipyridinium CH_2CH_2PO_3)Cl$ and 3 ml solution of 0.11M $K_2PdCl_4$ and $6.4 \times 10^{-3}M$ $K_2PtCl_4$ was heated to 60° C. for 30 minutes with constant stirring. The yellow solid so obtained was filtered and washed several times with water. This solid was resuspended in water and treated with $H_2$ gas as mentioned in the first synthesis. 0.0136 g of the dried solid was dissolved and analyzed as before, values in ppm: Zr=24.72; Pt=0.69; Pd=1.5

EXAMPLE 21

$Zr(O_3POH)(O_3PCH_2CH_2bipyridiniumCH_2CH_2PO_3)$ Cl.Pt.Pd-00:

200 mg of $Zr(O_3POH)(O_3PCH_2CH_2bipyridinium CH_2CH_2PO_3)Cl$ was treated with 1 ml of 0.11M $K_2PdCl_4$ and 0.18 ml of $1.6 \times 10^{-3}M$ $K_2PtCl_4$ and hydrogenated as mentioned in the previous example.). 0117 g of the final black solid was dissolved in conc. HCl, a few drops of conc. HNO3, and a few drops of 50% HF. This solution was diluted to 25 ml. The analysis of the solution is as follows: Zr(ppm)=48.92; Pt=not detected; Pd(ppm)=6.75.

EXAMPLE 22

$Zr(O_3POH)(O_3PCH_2CH_2bipyridiniumCH_2CH_2PO_3)$ Cl.Pt.Pd-30:

200 mg of $Zr(O_3POH)(O_3PCH_2CH_2bipyridinium CH_2CH_2PO_3)Cl$, 1 ml of $4.8 \times 10^{-2}M$ $K_2PdCl_4$, and 0.275 ml of $4.7×10^{-2}$M $K_2PtCl_4$ was stirred at 60° C. for 20 min. The yellow solid so obtained was filtered, washed with water, and hydrogenated as before. 0.0125 g of the solid was dissolved as before and diluted to 25 ml for analysis to give Zr=49.91 ppm, Pt=2.15 ppm, Pd=4.92 ppm

EXAMPLE 23

$Zr(O_3POH)(O_3PCH_2CH_2bipyridiniumCH_2CH_2PO_3)$ Cl.Pt.PD-11:

500 mg of $Zr(O_3POH)(O_3PCH_2CH_2bipyridinium$ $CH_2CH_2PO_3)Cl$ was refluxed for 6 hrs. with 15 ml of $7.4×10^{-3}$M $PdCl_2$ and 0.99 ml of $5.1×10^{-3}$M $K_2PtCl_4$. The solid was filtered, washed and as before. The hydrogenation of the solid was carried as before except for 1 hr. 0.0172 g of this solid was dissolved as before and diluted to 25 ml for analysis to give Zr=70.29 ppm; Pt=1.18 ppm; Pd=9.10 ppm

EXAMPLE 24

$Zr(O_3POH)(O_3PCH_2CH_2bipyridiniumCH_2CH_2PO_3)$ Cl.Pt.Pd-093:

500 mg of $Zr(O_3POH)(O_3PCH_2CH_2bipyridinium$ $CH_2CH_2PO_3)Cl$, 15 ml of $7.4×10^{-3}$M $PdCl_2$ and 0.99 ml of $5.1×10^{-3}$M $K_2PtCl_4$ was refluxed for 65 hrs. Filtered, washed, and hydrogenated as mentioned in the previous example. 0.018 g of the solid was dissolved as before and diluted to 25 ml for analysis to give Zr=127.98 ppm; Pt=0.78 ppm; Pd=7.72 ppm.

EXAMPLE 25

$Zr(O_3POH)(O_3PCH_2CH_2bipyridiniumCH_2CH_2PO_3)Cl.Pt$:

200 mg of $Zr(O_3POH)(O_3PCH_2CH_2bipyridinium$ $CH_2CH_2PO_3)Cl$ was treated with 2 ml of $5.1×10^{-3}$M solution of $K_2PtCl_4$ at 60° C. for 1 hr. The solid was filtered, washed, and hydrogenated as mentioned in the previous example. 0.0162 g of the solid was used to prepare a 25 ml solution for the analysis to give Zr=117.9 ppm; Pt=20.01 ppm

EXAMPLE 26

$Zr(O_3POH)(O_3PCH_2CH_2bipyridiniumCH_2CH_2PO_3)Cl.Pd$:

100 mg of $Zr(O_3POH)(O_3PCH_2CH_2bipyridinium$ $CH_2CH_2PO_3)Cl$ and 1 ml of $6.×10^{-2}$M $PdCl_2$ was treated at 60° C. for 4 hrs. The orange solid was filtered, washed, and hydrogenated as before. 0.0131 g of the solid was dissolved in 25 ml as mentioned above for analysis to give Zr=92.96 ppm; Pd=8.54 ppm The materials are grown on high surface area supports in a multi step process, as described below. Ion exchange can be carried out either as the film is growing or after it is prepared.

EXAMPLE 27

Synthesis of $SiO_2.Zr(O_3POH)(O_3PCH_2CH_2bipyridinium$ $CH_2CH_2PO_3)Cl.$:

One gram of silica gel (Selecto, Inc. Cat#162544, lot #216073) was heated at 200° C. for 1 hr. This was treated with 150 ml of 65 mM $ZrOCl_2$ at 60° C. for two days. This was followed by a treatment with 150 ml solution, which consists of 20 mM $(O_3PCH_2CH_2bipyridiniumCH_2CH_2PO_3)$ Cl, 20 mM phosphoric acid, and 60 mM NaCl at 60° C. for 18 hours. These treatments were repeated four times. At the end the pale yellow solid was washed with water and dried.

EXAMPLE 28

$SiO_2.Zr(O_3POH)(O_3PCH_2CH_2bipyridiniumCH_2CH_2PO_3)$ Cl.Pt.Pd-21:

270 mg of $SiO_2.Zr(O_3POH)(O_3PCH_2CH_2bipyridinium$ $CH_2CH_2PO_3)Cl$ was treated with 3 ml solution, which was 0.12M in $K_2PdCl_4$ and $6.4×10-3$M in $K_2PtCl_4$ at 60° C. for one Filtered and washed. The solid was hydrogenated as mentioned above. 0.0494 g of this solid was dissolved and in HCl, $HNO_3$, and 50 HF and diluted to 25 ml. Analyses: Zr=166.8 ppm, Pt=2.97 ppm, Pd=10.89 ppm.

EXAMPLE 29

Samples were prepared as described above in the synthesis of each compound in Examples 19–28. The metal content of these solutions were determined by ICP. The weight percent of viologen was estimated from the Zr value, assuming there are 2 Zr atoms per viologen molecule in the solid. The viologen unit was taken to be $C_{10}H_8N_2$. Resulting data is presented in Table 4 below.

TABLE 4

Elemental analyses of all compounds listed in this disclosure (ICP on dissolved samples). (% is weight percent)

| COMPOUND | R (obs) | R (theo) | % Pt | % Pd | % Zr |
|---|---|---|---|---|---|
| Du-D, sample 1 | 0.02 | 0.08 | 0.01 | 0.38 | 0 |
| DU-D, sample 2 | 0.08 | 0.093 | 0.02 | 0.23 | 0 |
| DU-F | 0.2 | 0.3 | 0.05 | 0.2 | 0 |
| DU-H | 0.65 | 0.7 | 0.15 | 0.08 | 0 |
| Zr*PV(POH)*Pd | 0 | 0 | 0 | 1.63 | 17.74 |
| Zr*PV(POH)*Pt*Pd-005 | 0 | 0.005 | not detected | 1.44 | 17.24 |
| Zr*PV(POH)*Pt*Pd-093 | 0.092 | 0.093 | 0.11 | 1.07 | 17.78 |
| Zr*PV(POH)*Pt*Pd-11 | 0.16 | 0.093 | 0.32 | 1.65 | 16.37 |
| Zr*PV(POH)*Pt*Pd-14 | 0.14 | 0.09 | 2.42 | 1.48 | 18.29 |
| Zr*PV(POH)*Pt*Pd-30 | 0.29 | 0.14 | 0.43 | 1.17 | 18.71 |
| Zr*PV(POH)*Pt*Pd-32 | 0.32 | 0.093 | 0.51 | 1.1 | 18.18 |
| Zr*PV(POH)*Pt*Pd-58 | 0.58 | 0.49 | 1.4 | 1.01 | 19.51 |
| Zr*PV(POH)*Pt | 1 | 1 | 3.09 | 0 | 18.19 |
| Zr*PV(POH)*Pd + PtCl$_4$ | 0.85 | Unknown | 3.86 | 0.66 | 46.56 |
| Zr*PV*Pt | 1 | 1 | 4.3 | 0 | 12.35 |
| Zr*PV(PH)*Pt | 1 | 1 | 7.96 | 0 | 14.87 |
| Zr*PV(POH)*Pt + PdCl$_4$ | 0.6 | Unknown | 2.35 | 1.57 | 16.55 |
| SiO$_2$*Zr*PV(POH)*Pt*Pd-11 | .11 | 0.093 | 0.1 | 0.78 | 8.06 |
| SiO$_2$*Zr*PV(POH)*Pt*Pd-21 | .21 | 0.093 | 0.15 | 0.5 | 8.7 |
| SiO$_2$*Zr*PV(POH)*Pt*Pd-27 | .27 | 0.093 | 0.35 | 0.9 | 2.67 |

Definitions for Table 1.:
DU-D: DuPont's U.S. Pat. No. 4,832,938 Table 1 A prep D; DU-F: DuPont's U.S. Pat. No. 4,832,938 Table 1 A prep. F; DU-H: DuPont's U.S. Pat. No. 4,832,938 Table 1 A prep. H.
Zr*PV(POH) = $Zr(O_3POH)(O_3PCH_2CH_2bipyridiniumCH_2CH_2PO_3)Cl$
Zr*PV(PH) = $Zr(O_3PH)(O_3PCH_2CH_2bipyridiniumCH_2CH_2PO_3)Cl$
Zr*PV = $Zr(O_3PCH_2CH_2bipyridiniumCH_2CH_2PO_3)Cl$
R = Pt/(Pt + Pd) (wt./wt.)
R(obs.) = The ratio calculated from the analysis of Pt and Pd by ICP.
R(theo) = The ratio calculated from the initial concentrations of Pt and Pd in the reacting solution.

HYDROGEN PEROXIDE FORMATION:

The materials of the present invention can be used as catalysts for the production of hydrogen peroxide. The process comprises treating an aqueous suspension of the catalyst with a source of oxygen and a source of hydrogen. Sources for oxygen include pure oxygen, air, ozone or any nitrogen oxide. The suspension can also contain acids or bases to control the pH of the system.

EXAMPLE 30

An amount of each of the catalysts was placed in a 50 mL plastic tube. 10 mL of 0.15 mM solution of acetanilide in 0.1M HCl was added to each tube, and it was sealed with a rubber septum. A mixture of oxygen and hydrogen was bubbled through the suspension. In some cases air was used rather than $O_2$. At sequential time intervals, starting at 1 hour (up to about 28 hours) the loss of solution volume due to evaporation was made up by the addition of 0.15 mM solution of acetanilide in 0.1M HCl and an amount of reaction mixture was withdrawn and diluted to 5 mL with titanium sulfate solution previously prepared in sulfuric acid. The absorbance of the solutions was recorded at 410 nm. The colorimetric assays have been checked by titration of the same solutions with $KMnO_4$ and shown to be very accurate. Table 4 shows the elemental analyses of compounds synthesized and/or used. The data shows the catalytic properties of the compounds in the production of hydrogen peroxide at various stages and under various conditions including different ratios of Pt to Pd and at a number of pHs.

The data listed in Table 5 represents $H_2O_2$ production for two preferred materials according to the present invention and some other catalysts. Table 6 shows similar test data for other compounds according to the present invention and other compounds. Table 7 shows data collected for several catalysts having different ratios of Pt to Pd. Table 8 shows data at a number of different pHs.

TABLE 5

Hydrogen peroxide formation, pH = 1 atm. The amount of catalysts used in each experiment was adjusted to give a constant number of moles of Pt + Pt in each experiment.

| Compound | Gas Ratio H2:O2 | Amount of Catalyst (mg) | Time (hrs.) | [H₂O₂] (mM) | Initial Turn- over # |
|---|---|---|---|---|---|
| Zr.PV(POH).Pt.Pd-093 | 1:1 | 22 | 1 | 12 | 10.8 |
| | | | 2.5 | 28 | |
| | | | 5 | 43 | |
| | | | 7 | 44 | |
| | | | 8.5 | 50 | |
| | | | 24 | 99 | |
| | 1:5 | 23 | 1.3 | 33 | 29.4 |
| | | | 2.3 | 51 | |
| | | | 4.6 | 71 | |
| | | | 6.3 | 79 | |
| | | | 8.3 | 80 | |
| | | | 24 | 140 | |
| | 1:10 | 22 | 1 | 10 | 8.8 |
| | | | 2.2 | 21 | |
| | | | 3.5 | 29 | |
| | | | 5.0 | 37 | |
| | | | 7.3 | 48 | |
| | | | 22 | 101 | |
| | 1:20 | 24 | 1 | 11 | 10 |
| | | | 2.4 | 28 | |
| | | | 4.2 | 39 | |
| | | | 5.7 | 53 | |
| | | | 8.2 | 71 | |
| | 1:40 | 23 | 1 | 2.4 | 2.4 |
| | | | 3.5 | 28 | |
| | | | 5.5 | 45 | |
| | | | 7.5 | 54 | |
| | | | 23 | 88 | |
| | | | 26 | 79 | |
| | | | 28 | 76 | |
| SiO₂.Zr.PV(POH).Pt.Pd-21 | 1:5 | 44 | 1 | 10 | 10 |
| | | | 2.5 | 22 | |
| | | | 4 | 31 | |
| | | | 6.5 | 33 | |
| | | | 8.3 | 33 | |
| | | | 9 | 33 | |
| DU-D, Sample 2 | 1:5 | 118 | 1 | 16 | 16 |
| | | | 2.9 | 31 | |
| | | | 3.9 | 38 | |
| | | | 5.9 | 49 | |
| | | | 7.9 | 58 | |
| | | | 23 | 77 | |
| DU-H | 1:5 | 128 | 1.1 | 16 | 16 |
| | | | 2.5 | 24 | |
| | | | 4 | 32 | |
| | | | 7.3 | 36 | |
| | | | 23 | 50 | |
| | | | 26 | 50 | |
| | | | 28 | 50 | |
| DU-F | 1:5 | 122 | 1 | 10 | 10 |
| | | | 2.3 | 19 | |
| | | | 4 | 30 | |
| | | | 6 | 44 | |
| | | | 9 | 58 | |
| | | | 24 | 46 | |

DU-D: DuPont's U.S. Pat. No. 4,832,938 Table 1 A prep. D.
DU-F: DuPont's U.S. Pat. No. 4,832,938 Table 1 A prep. F.
DU-H: DuPont's U.S. Pat. No. 4,832,938 Table 1 A prep. H.
Zr*PV(POH) = Zr(O₃POH)(O₃PCH₂CH₂bipyridiniumCH₂CH₂PO₃)Cl
Zr*PV(PH) = Zr(O₃PH)(O₃PCH₂CH₂bipyridiniumCH₂CH₂PO₃)Cl
Zr*PV = Zr(O₃PCH₂CH₂bipyridiniumCH₂CH₂PO₃)Cl
Pd-Pt-# refers to Pt/(Pt + Pd) (wt./wt.)

TABLE 6

Comparison of DuPont catalysts and novel catalysts according to the present invention using an H₂:O₂ ratio of 2:1 (O₂ from air) at pH = 1. The amount of catalyst used in each experiment was adjusted to give a constant number of moles of Pd + Pt in each experiment.

| COMPOUND | Quantity (mg) | H₂O₂ (mM) at 18 hours | H₂O₂ (mM) at 45 hours | Mole % Pd |
|---|---|---|---|---|
| DU-D | 152 | 4.6 | 1.0 | 0.545 |
| DU-F | 246 | 2.2 | 0.5 | 0.464 |
| DU-H | 262 | 4.6 | 4.5 | 0.200 |
| Zr.PV(POH)Pt.Pd-58 | 25 | 12.5 | 2.6 | 0.238 |
| Zr.PV(POH)Pt.Pd-32 | 38 | 22.5 | 15.1 | 0.394 |
| Zr.PV(POH)Pt.Pd-30 | 42 | 18.3 | 9.0 | 0.386 |
| Zr.PV(POH)Pt.Pd-00 | 43 | 13.7 | 10.1 | 0.584 |
| SiO₂.Zr.PV(POH)Pt.Pd-27 | 49 | 3.5 | 2.6 | 0.416 |
| Zr.PV.Pt | 25 | 0.5 | | |
| Zr.PV(PH).Pt | 40 | 0.6 | | |
| Zr.PV(POH).Pt | 30 | 5.5 | | |

DU-D: DuPont's U.S. Pat. No. 4,832,938 Table 1 A prep D.
DU-F: DuPont's U.S. Pat. No. 4,832,938 Table 1 A prep. F.
DU-H: DuPont's U.S. Pat. No. 4,832,938 Table 1 A prep. H.
Zr*PV(POH) = Zr(O₃POH)(O₃PCH₂CH₂bipyridiniumCH₂CH₂PO₃)Cl
Zr*PV(PH) = Zr(O₃PH)(O₃PCH₂CH₂bipyridiniumCH₂CH₂PO₃)Cl
Zr*PV = Zr(O₃PCH₂CH₂bipyridiniumCH₂CH₂PO₃)Cl
Pd-Pt-# refers to Pt/(Pt + Pd) (wt./wt.)

TABLE 7

$H_2O_2$ production from catalysts with different amounts of Pt (different R values) 2:1 mixture to $H_2:O_2$ (air was used as an oxygen source) 1 atm, pH = 1

| COMPOUND | Quantity (mg) | Time (hrs.) | $H_2O_2$ (mM) |
|---|---|---|---|
| Zr.PV(POH).Pt.Pd-005 | 28 | 1 | 2.2 |
| | | 23 | 2.5 |
| | | 27.5 | 2.5 |
| | | 30 | 2.7 |
| Zr.PV(POH).Pt.Pd-11 | 29 | 1 | 2.8 |
| | | 23 | 4.5 |
| | | 27.5 | 5.8 |
| | | 30 | 8.9 |
| Zr.PV(POH).Pt.Pd-093 | 56 | 1 | 4.2 |
| | | 7 | 7.7 |
| Zr.PV(POH).Pt.Pd-32 | 31 | 1 | 2.5 |
| | | 23 | 4.9 |
| | | 27.5 | 5.1 |
| | | 30 | 5.2 |
| Zr.PV(POH).Pt.Pd-58 | 30 | 1 | 2.2 |
| | | 23 | 3 |
| | | 27.5 | 2.9 |
| | | 30 | 2.9 |

Zr*PV(POH) = $Zr(O_3POH)(O_3PCH_2CH_2bipyridiniumCH_2CH_2PO_3)Cl$
Pd-Pt-# refers to Pt/(Pt + Pd) (wt./wt.)

TABLE 8

Altering pH with HCl, $H_2:O_2$ = 1:5, 1 atm using $Zr(O_3POH)(O_3PCH_2CH_2bipyridiniumCH_2CH_2PO_3)Cl.Pt.Pd-093$.

| pH | Quantity of Cmpd. (mg) | Time (hrs.) | $H_2O_2$ (mM) | Turnover # (total) |
|---|---|---|---|---|
| 1 | 23 | 1.3 | 33 | 29 |
| | | 2.3 | 51 | |
| | | 4.6 | 71 | |
| | | 6.3 | 79 | |
| | | 8.3 | 80 | |
| | | 24 | 140 | 125 |
| 2 | 22 | 1.3 | 18 | 17 |
| | | 3.3 | 68 | |
| | | 4.8 | 78 | |
| | | 5.8 | 80 | |
| | | 6.8 | 89 | 85 |
| 3 | 23 | 1.0 | 17 | 16 |
| | | 2.8 | 23 | |
| | | 4.0 | 23 | 21 |
| | | 6.3 | 19 | |

The above examples all involved atmospheric pressure reactions. Two parameters are important in this regard, those are the initial rate of hydrogen peroxide formation and the steady state concentration of hydrogen peroxide. The steady state concentration indicates the concentration at which the system is making water from peroxide at the same rate that peroxide is being formed, while the initial rate is an indication of the rate of hydrogen peroxide formation. The best steady state value observed was 140 mM (Table 5). At steady state the rate of oxygen reduction (equation 3) and hydrogen peroxide reduction (equation 4) are equal, so that the concentration of hydrogen peroxide is constant. The initial rate of the reaction in these experiments is 30 turnovers per hour (based on the moles of viologen present in the system). These experiments were carried out with a catalyst which has an R of 0.093 and a mixture of 1:5 of $H_2:O_2$. The best DuPont catalyst (DU-D) treated in an identical manner produced only 77 mM hydrogen peroxide at steady state. As the mixture of $H_2$ and $O_2$ is made richer in oxygen (i.e. $H_2:O_2$=1:10) the amount of hydrogen peroxide produced decreases.

Other catalysts loose a good fraction of their activity very quickly. To test this we took one sample of the catalyst and used it in several successive experiments. The results are shown in Table 9. To minimize hazards, a mixture of hydrogen and air was used in these experiments, so that the steady state values for the peroxide concentration are low relative to the numbers quoted above. The first three experiments show very similar level of peroxide production. The fourth experiment, shows a lower level of activity than the first three. This level of activity is still much higher than that observed for the DuPont catalyst under identical conditions. Elemental analysis shows that after the fourth cycle the weight % of Pt and Pd have gone up slightly, while the amount of Zr has gone down. This observation suggests that the decrease in activity has to do with partial dissolution of the metal phosphonate.

TABLE 9

Hydrogen Peroxide formation using Zr.PV(POH).Pt.Pd-093, pH = 1, $H_2:O_2$ = 2:1 (air used as $O_2$ source), pressure = 1 atm.

| Cycle # | time (hrs.) | $[H_2O_2]$ (mM) | total turnovers |
|---|---|---|---|
| 1st | 1 | 4.2 | 1.5 |
| | 2.5 | 4.3 | |
| | 5 | 6.1 | |
| | 7 | 7.7 | 2.8 |
| | 25 | 4.6 | |
| 2nd | 1 | 4.5 | 2.6 |
| | 2.8 | 9.8 | 5.6 |
| | 5.1 | 7.9 | |
| | 6.8 | 8 | |
| 3rd | 1 | 7.1 | 4.0 |
| | 5 | 10.7 | 6.1 |
| | 7 | 3.6 | |
| 4th | 1.2 | 4.2 | 2.4 |
| | 3 | 4.1 | |
| | 6 | 4.5 | 2.6 |

EXAMPLE 31

High Pressure Hydrogen Peroxide Formation: A number of experiments were performed with various combinations of gas pressures ($H_2$, $O_2$, $N_2$) in a 70 ml pressure vessel. Five mls of 0.1M HCl and 25 milligrams of $Zr(O_3POH)(O_3PCH_2CH_2bipyridiniumCH_2CH_2PO_3)Cl*Pt*Pd-14$ were added to the vessel. A mixture of oxygen, hydrogen, and nitrogen at the prescribed pressures was added to the vessel. The reactions were allowed to proceed for various times. (TABLE 10). The $H_2O_2$ concentrations are similar to those obtained in experiments at atmospheric pressure (see above). The data shows that an increase in either reactor vessel volume or an increase in pressure would yield higher $H_2O_2$ concentrations, i.e., if $P_{H2}$ and $P_{O2}$ were increased by a factor of 5 the results would be one molar $H_2O_2$ (see e.g., example 2 in Table 10).

TABLE 10

| Time (hrs) | $[H_2O_2]$ final (moles/L) | Total pressure (psi) | $P_{O2}$ (psi) | $P_{H2}$ (psi) | $P_{N2}$ (psi) | Moles $H_2$ in system | Yield of $H_2O_2$ relative to $H_2$ in system |
|---|---|---|---|---|---|---|---|
| 15 | 0.143 | 175 | 100 | 15 | 60 | 0.0029 | 25% |
| 23 | 0.214 | 175 | 100 | 15 | 60 | 0.0029 | 37% |
| 48† | 0.410 | 175 | 100 | 15 | 60 | | |
| 18 | 0.084 | 150 | 120 | 6 | 24 | 0.0011 | 38% |
| 13 | 0.062 | 150 | 120 | 6 | 24 | 0.0011 | 28% |

†After 24 hours the system was vented and a fresh charge of the same gas mixture was added, then allowed to react for another 24 hours.

EXAMPLE 32

Synthesis of phosphonate derivatized Polymer template:

Diethyl-4-bromobutylphosphonate was made by the Michealis-Arbuzov Rearrangement of $Br(CH_2)_4Br$ with triethyl phosphite. 1,4-dibromobutane (21.5 g, 100 mmol) and triethylphosphite (6.65 g, 40 mmol) were heated to 150° C. for 6 hours. Unreacted 1,4-dibromobutane was removed by vacuum distillation.

Poly(4-vinylpyridine) (PVP) was alkylated with diethyl 4-bromobutyl phosphonate to give polymers (PVP-$C_4$P). PVP (1 g, 9.5 mmol) was dissolved in 60 mL N,N-dimethyl formamide (DMF) with 1.48 g (5.4 mmol) of diethyl-4-bromobutylphosphonate. The mixture was stirred at 60° C. for two hours, and DMF was removed under vacuum. The remaining solid was washed with a 1:4 (v:v) mixture of methanol and diethyl ether, and then refluxed in ether for two hours. The solid sample was filtered and dried. The dried sample was then dissolved in 30 mL methylene chloride, 12 g of bromotrimethylsilane was added and the mixture was stirred for 6 hours under an Ar atmosphere. $H_2O$ (80 mL) was added and the solution was stirred one more hour. The water phase was separated, and removed under vacuum to get yellow-brown solid (PVP-$C_4$P). CHN analysis of PVP-$C_4$P gave C: 55.76, H: 6.67, N: 8.20. This analysis is consistent with 25% of the pyridyl groups being alkylated. $[C_7H_7N]_3[C_{11}H_{17}NO_3PBr]*3H_2O$ would give a CHN analysis of C: 55.57, H: 6.41, N: 8.10. The NMR spectra of PVP-$C_4$P consists of relatively broad lines, due to the polymeric nature of the material. Three broad appear in the 1H NMR spectrum in d6-DMSO/$D_2O$ at 8.2, 6.6 and 1.6 ppm, with integrated intensities of 1, 1, and 2.4. This ratio is consistent with the 25% derivatization if the two downfield peaks are assigned to pyridyl/pyridinium resonances and the peak at 1.6 ppm is assigned to all of the $CH_2$ groups except the one bound to nitrogen (based on model compounds the latter peak is expected to fall under HDO), since this should give a ratio of 1:1:2.3.

EXAMPLE 33

Platinum colloids were prepared via reduction of hexachloroplatinate solution by sodium citrate. The reduction was similar to that described by Brugger, et. al., except that the temperature was held at 90° C. in order to get uniform particle size (P. Brugger, P. Cuendet, M. Gatzel, J. Am. Chem. Soc., (1981), 103, page 2923.) $K_2PtCl_6$ (40 mg) was dissolved in 300 mL distilled water and the solution was heated to 90° C. An aqueous solution of sodium citrate (30 mL, 1% weight percent sodium citrate) was added and the solution stirred for 3 hours. After the colloid suspension was cooled to room temperature, Amberlite-MB-1 exchange resin was added and the mixture was stirred to remove the excess citrate until the conductivity of the solution was less than 5 m S/cm.

EXAMPLE 34

Growth of zirconium viologen-bisphosphonate (ZrVP) on PVP-$C_4$P:

Polymer PVP-$C_4$P (5 mg) was dissolved in 50 mL of the Pt colloid suspension described above. The weight ratio of Pt:polymer is 1:2.5. After the mixture was shaken for one hour to reach equilibrium, 0.3 gm of $ZrOCl_2 \cdot 8H_2O$ was dissolved in the PVP-$C_4$P/Pt suspension. The mixture was shaken at room temperature overnight in order to complete the reaction of $Zr^{4+}$ ions with phosphonate groups of the polymer. The mixture was then dialyzed against distilled water to remove free ions. The molecular weight cut of the dialysis tube used here was 12,000–15,000.

Dialysis was carried out until conductivity of the water was less than 5 mS/cm. The suspension was poured back to a flask, 0.04 g viologen bisphosphonic acid was added and the mixture was shaken at 60° C. overnight, a similar dialysis process was carried out to a conductivity of less than 5 mS/cm. The zirconium and bisphosphonate treatments were repeatedly performed up to five times in order to grow multiple layers of the ZrVP materials.

EXAMPLE 35

Photochemical Hydrogen Generation:

Photochemical hydrogen generation was carried out by irradiating samples of the polymer templated ZrVP on Pt colloids (Example 34) in EDTA solutions. The suspension was held in a 1 cm square cell kept at 20° C. throughout the photochemical experiment. A mixture of 4 mL of the sample suspension and 1 mL of 0.1M NaEDTA (sacrificial reducing agent) were thoroughly degassed by bubbling $N_2$ through the suspension prior to photolysis. The sample was then irradiated with a 200 Watt Hg/Xe arc lamp. Levels of hydrogen were measured by GC.

Photolysis of a suspension sample with 11 mg ZrPV(Cl) in 0.05M NaEDTA by a 200-w Hg/Xe lamp leads to a hydrogen production rate 0.25 mL/hr for the first hour. EDTA is used as a sacrificial reductant to turn the system over. The rate of hydrogen production gradually decrease on longer irradiation time. This is similar to that on multi layer thin films grown on silica surface.

Passing the light through a 260 nm cutoff filter decreases the rate of hydrogen production by about 50%, but produces about 20% more hydrogen in longer period of time. The wave length dependence for photoproduction of hydrogen in this system correlates well with that observed in forming charge-separated state in both microcrystalline and thin film sample of ZrPV(Cl).

EXAMPLE 36

Sample and substrate preparation:

Polymer PVP-$C_4$P (molecular weight=100,000) was synthesized from poly(4-vinylpyridine) and diethyl,4-bromobutyl-phosphonate by the method described in Example 32. $H_2O_3PCH_2CH_2$(bipyridinium)$CH_2CH_2PO_3H_2Cl_2$ (V2P) was prepared as described in Example 1. Single-crystal polished silicon wafers (~1×3 $cm^2$) and microscopic fused silica (quartz) slides (~1×3 $cm^2$) and 0.05–0.1 mm thick gold, platinum and palladium foil (~1× 0.5 $cm^2$) were each used as substrates. They were cleaned before use with a mixture of concentrated $H_2SO_4$ and 30% $H_2O_2$ (v/v 3:1), rinsed thoroughly with distilled water and heated at 500° C. overnight to provide a dehydroxylated surface.

Surface initialization procedure:

A silicon wafer, quartz slide or metal foil strip was dipped into an aqueous 0.5% (w/w) solution of PVP-$C_4$P. After 5 minutes, the slide was removed from the solution and dried by blowing pure $N_2$. A thin layer of 80 mM solution of $ZrOCl_2$ was applied to the surface of the slide to achieve the cross-linking of phosphonic acid residues of polymer, and the film was air-dried. To make sure that the polymer was fully cross-linked with $Zr^{4+}$ ions, the process was repeated twice. The slide was then washed with distilled water to remove extra ions from surface.

Film growth:

Multilayers of ZrPV(Cl) compound were produced on the zirconium rich surfaces by repeated dipping of the initialized substrate in 10 mM V2P aqueous solution at 80° C. for 4 hours (step 1), then in 60 mM ZrOCl$_2$ aqueous solution at room temperature for 2 hours (step 2). The surface was thoroughly rinsed with distilled water between dippings (step 3). Steps 1–3 constituted one cycle of treatment. Various films were made by repeating up to 15 cycles. In the last cycle step 2 was usually omitted.

EXAMPLE 37

Atomic force microscopic (AFM) images were obtained with NanoScope III Scanning Probe Microscope (Digital Instruments). Surface was imaged in a tapping mode with silicon cantilevers (typical $F_o$ 320–360 kHz). AFM images (0.5×0.5 µm2) of the samples reveal their finer features and demonstrate that the structure and thickness of the films prepared in the same way depends on the nature of the substrate. All of the samples showed a significant increase in RMS roughness on fill growth.

Examination of the AFM images shows that in all case the materials growing on the surface consist of microcrystallites. It is in contrast to the growth of Zn and Cu alkanebisphosphonate multilayer films (Yang, H. C., K. Aoki, H.-G. Hong, D. D. Sackett, M. F. Arendt, S.-L. Yau, C. M. Bell, T. E. Mallouk J. Am. Chem. Soc. 1993, 115, 11855–11862.) which results in the smoothing of surface roughness. The crystals are smaller in the case of quartz and silicon substrates and larger in the case of metals. There seems to be no direct correlation between the overall roughness of the fill and the crystal size, as well as between the roughness of the bare substrate and of the film on it. The films on quartz consist of small crystals uniformly distributed on the surface. Films on gold and platinum are made up of somewhat larger crystals than those on quartz, but they are still uniformly distributed on gold and tend to aggregate into larger clusters on platinum. Growth of films on Pd leads to large crystals, which appear clustered into even larger islands. In contrast, films on silicon consist of very small particles, which also cluster into large islands. No differences were observed in the AFM images of untreated and PVP-C$_4$P treated substrates.

EXAMPLE 38

Cyclic voltammograms (CV) were registered at Au, Pt and Pd electrodes (working surface area ~0.3 cm$^2$) covered with ZrPV(Cl) films as described above in Examples 36–37. PAR Potentiostat/Galvanostst Model 283 was used. A counter electrode (Pt wire) was separated from the working aqueous 0.1M KCl solution by a porous glass frit. The reference was a saturated calomel electrode (SCE). Oxygen was removed from the working solution by bubbling with argon gas of high purity.

Cyclic voltammograms of the ZrPV(Cl) films at the Au, Pt and Pd electrodes show broad peaks with reduction potentials ($E_{surf}°=(E_{p,c}+E_{p,a})/2$, where $E_{p,c}$ and $E_{p,a}$ are the cathodic and anodic peak potentials, respectively) close to –0.77 V, with peak-to-peak separations (ΔE) of 120–200 mV. ΔE is slightly affected by the number of treatments on gold and platinum but shows no change for palladium. This large ΔE increasing as the experimental time scale is shortened (at higher potential scan rates) indicates the kinetic limitations for charge transfer which are more serious for anodic processes and for Pt and Pd electrodes.

Integration of the reduction peaks at the cyclic voltammograms confirm that the amount of ZrPV(Cl) accumulated at the surface after the same number of treatments is different for different substrates. Much more material is being accumulated at Pt and Pd than at Au. These results are consistent with the AFM data indicating that films at Pt and Pd are more rough than at Au. Estimates based on the integrals obtained from the cyclic voltammograms indicate that every cycle of treatment results not in a single layer coating but adds 3–6 layers depending on substrate.

The $E_{surf}°$ values are 100 mV more negative than $E°$ for the one-electron reduction of V2P in aqueous solution which we found to be –0.67 V (ΔE=70 mV), which is close to the redox potential reported for the methylviologen dication/cation radical redox couple (–0.69 V). The 100 mV shift of $E_{surf}°$ to the more negative values in films as compared to V2P in solution is not significantly affected by the number of times the substrate is treated with the Zr$^{4+}$ and viologen bisphosphonate.

EXAMPLE 39

Blue color due to photochemical charge separation is observed on the layered ZrPV(Cl) with polysoap template, if the sample is photolyzed with a 200 w Hg/Xe lamp in vacuum or under N$_2$. Five minute photolysis leads to the formation of both reduced viologen monomer and dimmer on the irradiated sample. Electron spectra show the decreasing band of 270 nm, and appearance of bands at 405, 605 nm and 380, 540 nm, which are correspond to monomer and dimmer respectively. The electronic spectra of the ZrPV(Cl) with polysoap template, as well as the air sensitivity of the photoreduced sample suggest that this multilayered compound is not as tightly packed as microcrystalline samples of ZrPV(Cl).

Treating of a photoreduced suspension sample of layered ZrPV(Cl) with template with air leads to complete bleaching within a matter of seconds, while the microcrystalline samples require hours to days. Oxygen appears to freely diffuse through the more open lattice of the compound. This is probably related to the flexible blanket-like feature of the materials with template.

EXAMPLE 40

Synthesis of 1,4-Bis(4-phosphonobutylamino)benzene (PAPD).

(H$_2$O$_3$P—(CH$_2$)$_4$—NHC$_6$H$_4$NH—(CH$_2$)$_4$—PO$_3$H$_2$).

5.0 g. (0.046 moles) of p-phenylendiamine and 15.6 g. (0.114) of diethyl 4-bromobutyl phosphonate were refluxed in 50 mL of THF in the presence of 1.56 g. of NaH for 2 days. After cooling, 50 mL of H$_2$O were slowly added to the reaction mixture. The solution was extracted three times with 100 mL portions of CHCl$_3$. TLC showed the desired product was in the CHCl$_3$ layer. Decolorizing charcoal was added to the CHCl$_3$ solution and stirred for 1 hr then filtered. The CHCl$_3$ solution was taken to dryness leaving a brown oil. $^1$H NMR (D$_2$O), 6.9(4H, s), 3.1(4H, t), 1.5(12H, m) ppm. Mass Spectrum: E.I., M$^{+1}$ meas.=492, M$^{+1}$ theor.=492; major fragments: 446, 354, 193, 137, 125. The ester was hydrolyzed to the acid by refluxing in 6M HCl for two days. The acid was precipitated from this solution by the addition of acetone.

EXAMPLE 41

Synthesis of viologen bisphosphonic acid salts [N,N'-bis(2-phosphonoethyl)-4,4'-bipyridine dihalide] (PV(X)):

(H$_2$O$_3$P—(CH$_2$)$_2$-4,4'-bipyridinium-(CH$_2$)$_2$—PO$_3$H$_2$).

The viologen dichloride salt was prepared by reacting 1.2 g. (6.0 mmoles) of diethyl (2-chloroethyl) phosphonate with 0.47 g. (3.0 mmoles) of 4,4'-bipyridine in 120 mL of H₂O at 110° C. for 40 hours. The ester was converted to the acid by refluxing in 6M HCl. The viologen dibromide salt was prepared as above except diethyl-2-bromoethylphosphonate was used. The ester was dried under vacuum then converted to the acid by overnight stirring with a three fold excess of bromotrimethyl silane in dry acetonitrile followed by the addition of water. The viologen diiodide salt was prepared by adding AgPF₆ to a solution of the viologen dichloride salt to precipitate AgCl. When the viologen dihexafluorophosphate salt was isolated, an excess of KI was added to the solution. The resulting reddish-brown solid was isolated by filtration. All viologen salts were purified by dissolving in a minimum volume of water and precipitated by the slow addition of isopropyl alcohol. ¹H NMR of all salts, (D₂O), 9.1(4H, d), 8.5(4H, d), 4.2(4H, m), 2.0(4H, m) ppm.

EXAMPLE 42

Synthesis of 4,4'-bis(2-phosphonoethyl)biphenyl (EPB): (H₂O₃P—(CH₂)₂-(4,4'-biphenyl)-(CH₂)₂—PO₃H₂).

In a dry glass pressure tube were added 3.8 g. (9.4 mmol) diiodobiphenyl, 3.23 g. (20 mmol) diethyl vinylphosphonate, 0.05 g. (0.2 mmol) palladium acetate and 0.23 g. (0.7 mmol) tritolylphosphine dissolved in 20 mL dry triethylamine and 30 mL dry toluene. Mixture was purged with Ar for 10 min then closed. Reaction was heated to 110° C. with stirring for 24 hrs. Approximate yield of 4,4'-bis (diethyl vinyl phosphonate)biphenyl was 30%. ¹H NMR (DMSO), 7.8 (8H, m), 7.4 (2H, d), 6.5 (2H, t), 4.0 (8H, m), 1.2 (12H, t) ppm. Mass Spectrum: E.I., M⁺¹ meas.=478, M⁺¹theor.=478; major fragments: 369, 341, 313, 231, 202. This intermediate was hydrogenated with Pd/C in methanol. To the ester were added 20 mL dry CH₂Cl₂ and 1 mL bromotrimethyl silane. After the addition of water and separation with ether, the acid was isolated. ¹H NMR (CDCl₃), 7.4(8H, d), 2.9(4H, m), 2.1(4H, m) ppm.

EXAMPLE 43

Synthesis of N,N'-bis(2-phosphonoethyl)-4,4'-bis(4-vinyl pyridine)biphenyl dichloride (VPB):

(H₂O₃P—(CH₂)₂—NC₅H₄—CH=CH—(4,4'-biphenyl)—CH=CH—C₅H₄N—(CH₂)₂—PO₃H₂).

In a dry glass pressure tube were added 1.04 g. (2.6 mmol) diiodobipbenyl, 3.0 mL (27 mmol) vinyl pyridine, 0.09 g. (0.36 mmol) palladium acetate and 0.2 g. (0.6 mmol) tritolylphosphine dissolved in 8 mL dry triethylamine and 20 mL dry acetonitrile. Mixture was purged with Ar for 15 min then closed. Reaction was heated to 110° C. with stirring for 48 hrs. Approximate yield of 4,4'-bis(4-vinyl pyridine) biphenyl was 30%. ¹H NMR (CDCl₃), 8.9 (4H, d), 8.2 (4H, d), 8.1 (4H, d), 7.9 (4H, d), 7.6 (4H, d) ppm. Mass Spectrum: E.I., M⁺¹ meas.=360, M⁺¹ theor.=360; major fragments: 266, 180, 91.0.3 g. (0.83 mmol) of this were combined with 0.5 g. (2.0 mmol) diethyl-2-bromoethyl phosphonate in a round bottom flask and dissolved in 10 mL DMF. Mixture was heated at 90° C. for 16 hrs until a yellow precipitate was observed. DMF was vacuum distilled and the yellow ester was obtained. To the ester were added 10 mL dry CH₂Cl₂ and 1 mL bromotrimethyl silane. Mixture was stirred for 12 hrs then H₂O was added causing am orange precipitate. Solid was isolated and recrystallized from H₂O by the slow addition of cold methanol. NMR showed the disappearance of the ester peaks indicating the acid was formed. ¹H NMR (DMSO), 8.42 (4H, d), 8.22 (4H, d), 7.55 (8H, m), 7.04 (4H, d), 4.26 (4H, t), 1.41 (4H, t) ppm.

EXAMPLE 44

Preparation of Au/4(ZrAV2P) photoelectrode:

Gold foil (0.1 mm thick) was cut into pieces 2×50 mm2 and cleaned in a concentrated HNO3 for 10 min, then thoroughly rinsed with distilled water and 100% ethanol. Self-assembled films of (3-mercaptopropyl) trimethoxysilane (3-MPT) were formed by immersion of Au foil into solution of 20 mM 3-MPT in 100% ethanol for 2 hours at room temperature. (See e.g., W. R. Thompson, J. E. Pemberton, *Thin Sol-Gel Silica Films on (3-Mercaptopropyl)trimethoxysilane modified Ag and Au electrodes*, Chem. Mater. 7, 130–136 (1995)). Then Au was rinsed with 100% ethanol and allowed to air-dry. Hydrolysis of the 3-MPT modified surface was then achieved by immersion into an aqueous 0.1M solution of HCl for 12 hours at room temperature. The surface was zirconated by dipping the foil into 60 mM ZrOCl2 aqueous solution for 2 hours at room temperature.

AV2P (H₂O₃P—(CH₂)—C₆H₄—NC₅H₄—C₅H₄N—C₆H₄—(CH₂)—PO₃H₂) was synthesized using standard literature procedures. The ZrAV2P fill was grown by alternate treatment in 10 mM AV2P solution at 80° C. for 4 hours and then in 60 mM ZrOCl2 aqueous solution at room temperature for 2 hours. These 2 steps were each repeated 4 times (4 cycles of deposition).

EXAMPLE 45

Photochemistry of film of Example 44

Photoelectrochemical measurements were performed in a quartz cell containing 0.1M NaClO4 (supporting electrolyte) and 10-2M Eu(NO3)3 (electron acceptor). Dark currents and photocurrents were measured with PAR M283 Potentiostat/Galvanostat using M270 chronoamperometry software.

A Au/4(ZrAV2P) electrode prepared in Example 44 was used as a working electrode, with Pt serving as a counter electrode (2 electrode circuit), and, in a separate measurement, with SCE as a reference electrode and Pt as a counter electrode (3 electrode circuit). The Au/4(ZrAV2P) electrode was illuminated with 200 W Hg/Xe lamp with a filter cutting off UV light below 360 nm. Illuminated area of the electrode was ~0.5 cm2.

Figure 5:
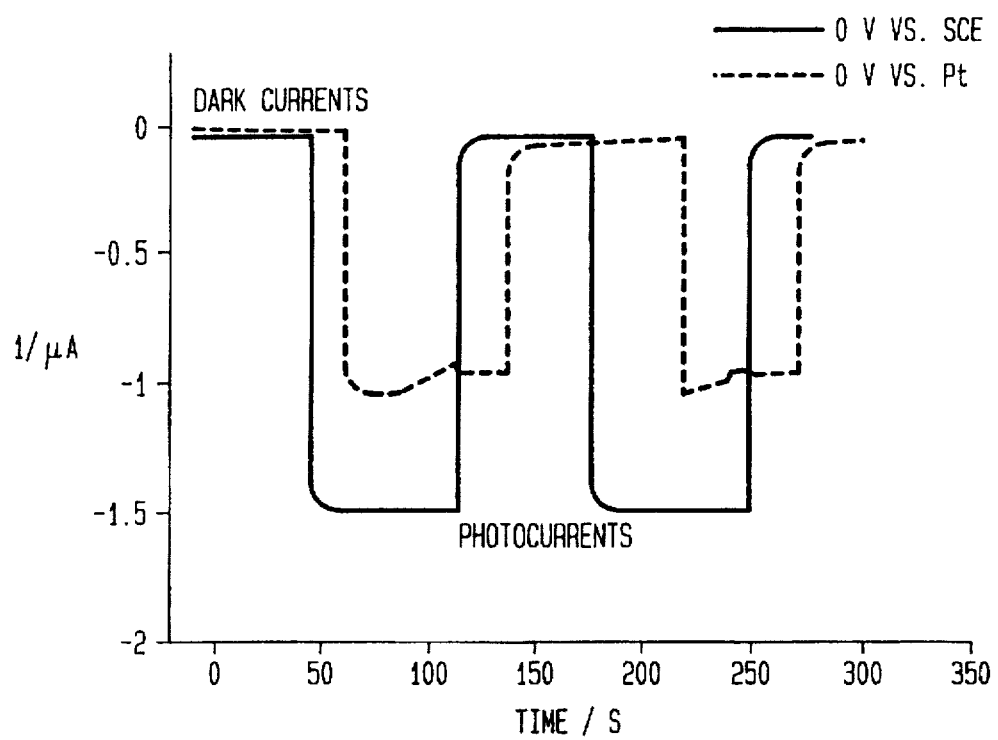
FIG. 5. is a graph of the photochemical measurements of films of Example 45.

The results of these tests are shown in the graph of FIG. 5

EXAMPLE 46

Photochemistry of film of Example 44

Photoelectrochemical measurements were performed in a quartz cell containing 0.1M NaClO4 (supporting electrolyte) and 10-2M Eu(NO3)3 (electron acceptor). Dark currents and photocurrents were measured with PAR M283 Potentiostat/Galvanostat using M270 chronoamperometry software.

A Au/4(ZrAV2P) electrode prepared in Example 44 was used as a working electrode, with Pt serving as a counter electrode (2 electrode circuit), and, in a separate measurement, with SCE as a reference electrode and Pt as a counter electrode (3 electrode circuit). The Au/4(ZrAV2P) electrode was illuminated with 200 W Hg/Xe lmp. Illuminated area of the electrode was ~0.5 cm2.

Figure 6:
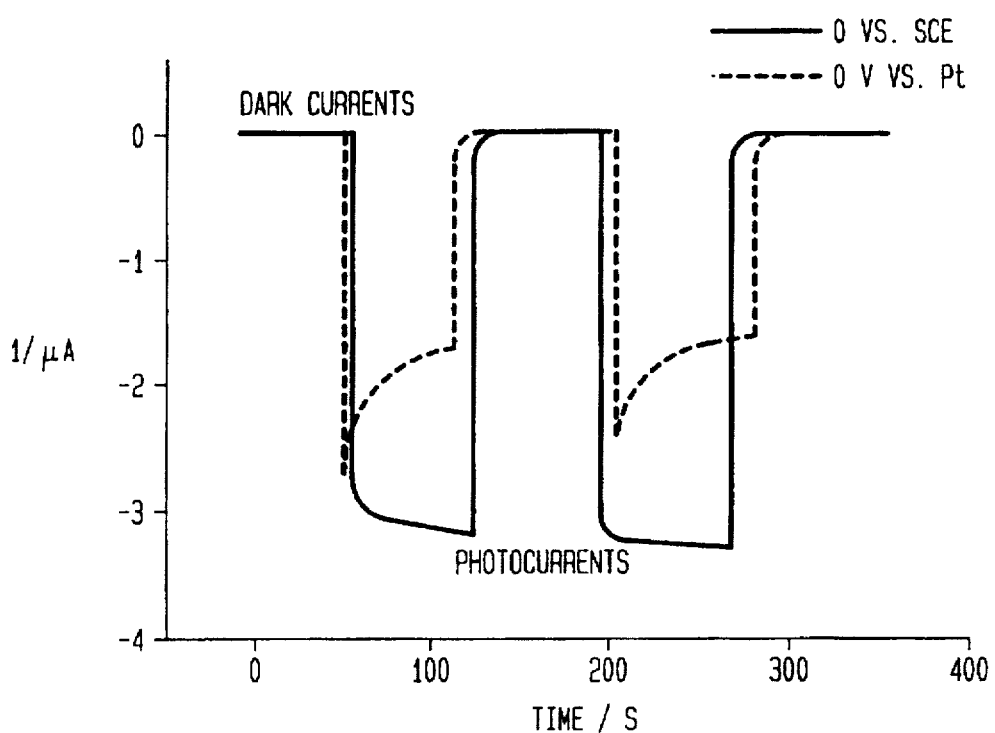
FIG. 6. is a graph of the photochemical measurements of films of Example 46.

The results of these tests are shown in the graph of FIG. 6.

EXAMPLE 47

Preparation of Au/4(ZrDABP)/4(ZrAV2P) photoelectrode:

Gold foil (0.1 mm thick) was cut into pieces 2×50 mm2 and cleaned in a concentrated HNO3 for 10 min, then thoroughly rinsed with distilled water and 100% ethanol. Self-assembled films of (3-mercaptopropyl) trimethoxysilane (3-MPT) were formed by immersion of Au foil into solution of 20 mM 3-MPT in 100% ethanol for 2 hours at room temperature. (See e.g., W. R. Thompson, J. E. Pemberton, *Thin Sol-Gel Silica Films on (3-Mercaptopropyl)trimethoxysilane modified Ag and Au electrodes*, Chem. Mater. 7, 130–136 (1995)). Then Au was rinsed with 100% ethanol and allowed to air-dry. Hydrolysis of the 3-MPT modified surface was then achieved by immersion into an aqueous 0.1M solution of HCl for 12 hours at room temperature. The surface was zirconated by dipping the foil into 60 mM ZrOCl2 aqueous solution for 2 hours at room temperature.

DABP ($H_2O_3P$—($CH_2$)—$C_6H_4$—N=N—$C_6H_4$—($CH_2$)—$PO_3H_2$) was synthesized using standard literature procedures. ZrDABP/ZrAV2P film was grown by alternate treatment in 10 mM DABP solution at 80° C. for 4 hours and in 60 mM ZrOCl2 aqueous solution at room temperature for 2 hours (4 cycles of deposition), then by alternate treatment in 10 mM AV2P solution at 80° C. for 4 hours and in 60 mM ZrOCl2 aqueous solution at room temperature for 2 hours (next 4 cycles of deposition).

EXAMPLE 48

Photochemistry of film of Example 47

Photoelectrochemical measurements were performed in a quartz cell containing 0.1M NaClO4 (supporting electrolyte) and 10-2M Eu(NO3)3 (electron acceptor). Dark currents and photocurrents were measured with PAR M283 Potentiostat/ Galvanostat using M270 chronoamperometry software.

A Au/4(ZrDABP)/4(ZrAV2P) electrode prepared in Example 47 was used as a working electrode, with Pt serving as a counter electrode (2 electrode circuit), and, in a separate measurement, with SCE as a reference electrode and Pt as a counter electrode (3 electrode circuit). The Au/4(ZrDABP)/4(ZrAV2P) electrode was illuminated with 200 W Hg/Xe lamp with a filter cutting off the UV light below 420 nm. Illuminated area of the electrode was ~0.5 cm2.

Figure 7:
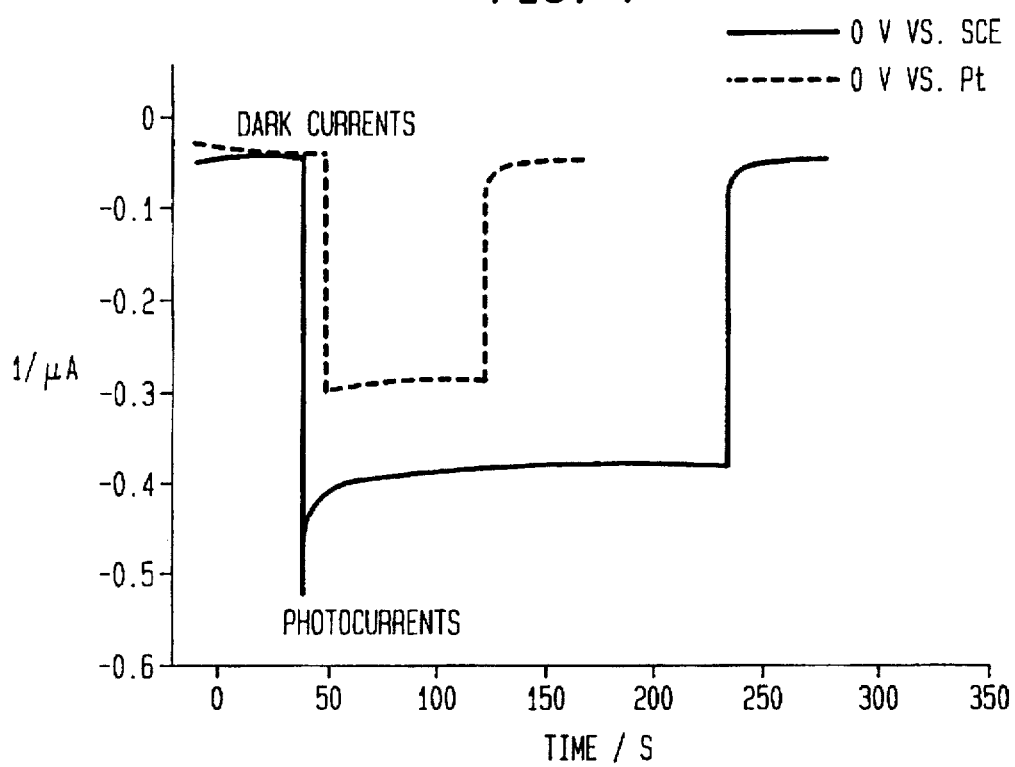
FIG. 7. is a graph of the photochemical measurements of films of Example 48.

The results of these tests are shown in the graph of FIG. 7.

EXAMPLE 49

Photochemistry of film of Example 47

Photoelectrochemical measurements were performed in a quartz cell containing 0.1M NaClO4 (supporting electrolyte) and 10-2M Eu(NO3)3 (electron acceptor). Dark currents and photocurrents were measured with PAR M283 Potentiostat/ Galvanostat using M270 chronoamperometry software.

A Au/4(ZrDABP)/4(ZrAV2P) electrode prepared in Example 47 was used as a working electrode, with Pt serving as a counter electrode (2 electrode circuit), and, in a separate measurement, with SCE as a reference electrode and Pt as a counter electrode (3 electrode circuit). The Au/4(ZrDABP)/4(ZrAV2P) electrode was illuminated with 200 W Hg/Xe lamp with a filter cutting off the UV light below 360 nm. Illuminated area of the electrode was ~0.5 cm2.

EXAMPLE 50

Photochemistry of film of Example 47

Photoelectrochemical measurements were performed in a quartz cell containing 0.1M NaClO4 (supporting electrolyte) and 10-2M Eu(NO3)3 (electron acceptor). Dark currents and photocurrents were measured with PAR M283 Potentiostat/ Galvanostat using M270 chronoamperometry software.

A Au/4(ZrDABP)/4(ZrAV2P) electrode prepared in Example 47 was used as a working electrode, with Pt serving as a counter electrode (2 electrode circuit), and, in a separate measurement, with SCE as a reference electrode and Pt as a counter electrode (3 electrode circuit). The Au/4(ZrDABP)/4(ZrAV2P) electrode was illuminated with 200 W Hg/Xe lamp. Illuminated area of the electrode was ~0.5 cm2.

Figure 8:
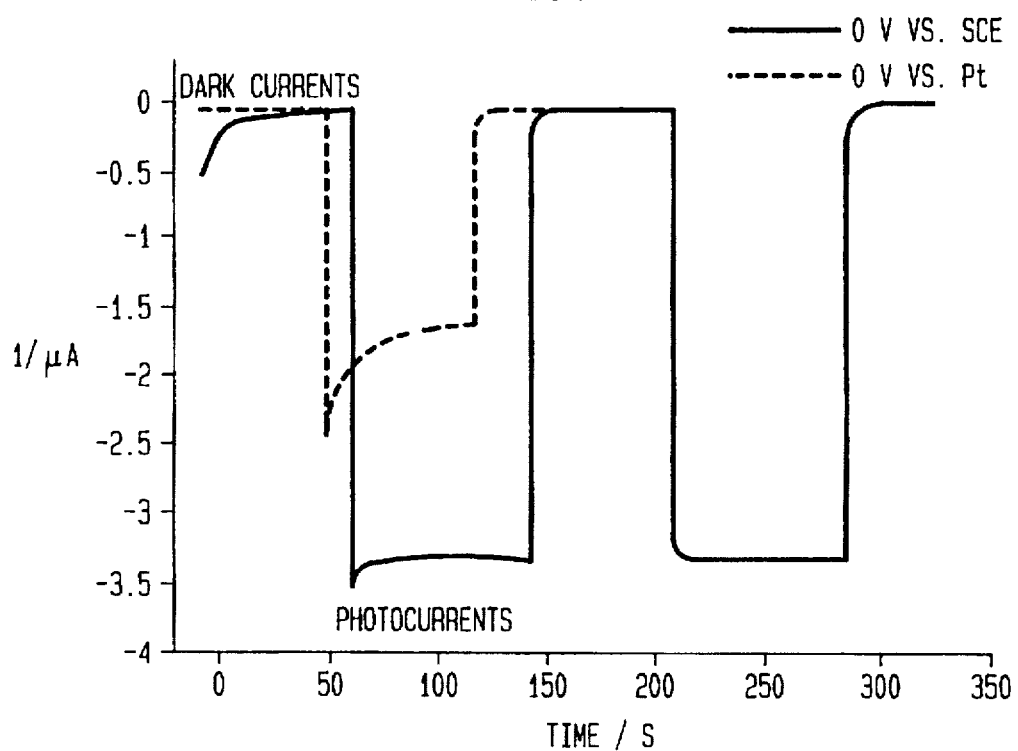
FIG. 8. is a graph of the photochemical measurements of films of Example 50.

The results of these tests are shown in the graph of FIG. 8.

EXAMPLE 51

Preparation of Au/4(ZrPAPD)/4(ZrAV2P) photoelectrode:

Gold foil (0.1 mm thick) was cut into pieces 2×50 mm2 and cleaned in a concentrated HNO3 for 10 min, then thoroughly rinsed with distilled water and 100% ethanol. Self-assembled films of (3-mercaptopropyl) trimethoxysilane (3-MPT) were formed by immersion of Au foil into solution of 20 mM 3-MPT in 100% ethanol for 2 hours at room temperature. (See e.g., W. R. Thompson, J. E. Pemberton, *Thin Sol-Gel Silica Films on (3-Mercaptopropyl)trimethoxysilane modified Ag and Au electrodes*, Chem. Mater. 7, 130–136 (1995)). Then Au was rinsed with 100% ethanol and allowed to air-dry. Hydrolysis of the 3-MPT modified surface was then achieved by immersion into an aqueous 0.1M solution of HCl for 12 hours at room temperature. The surface was zirconated by dipping the foil into 60 mM ZrOCl2 aqueous solution for 2 hours at room temperature.

ZrPAPD/ZrAV2P film was grown by alternate treatment in 10 mM PAPD solution at 80° C. for 4 hours and in 60 mM ZrOCl2 aqueous solution at room temperature for 2 hours (4 cycles of deposition), then by alternate treatment in 10 mM AV2P solution at 80° C. for 4 hours and in 60 mM ZrOCl2 aqueous solution at room temperature for 2 hours (next 4 cycles of deposition).

EXAMPLE 52

Photochemistry of film of Example 51

Photoelectrochemical measurements were performed in a quartz cell containing 0.1M NaClO4 (supporting electrolyte) and 10-2M Eu(NO3)3 (electron acceptor). Dark currents and photocurrents were measured with PAR M283 Potentiostat/ Galvanostat using M270 chronoamperometry software.

A Au/4(ZrPAPD)/4(ZrAV2P) electrode prepared in Example 51 was used as a working electrode, either with Pt serving as a counter electrode (2 electrode circuit), or with SCE as a reference electrode and Pt as a counter electrode (3 electrode circuit). The Au/4(ZrPAPD)/4(ZrAV2P) electrode was illuminated with 200 W Hg/Xe lamp. Illuminated area of the electrode was ~0.5 cm2.

Figure 9:
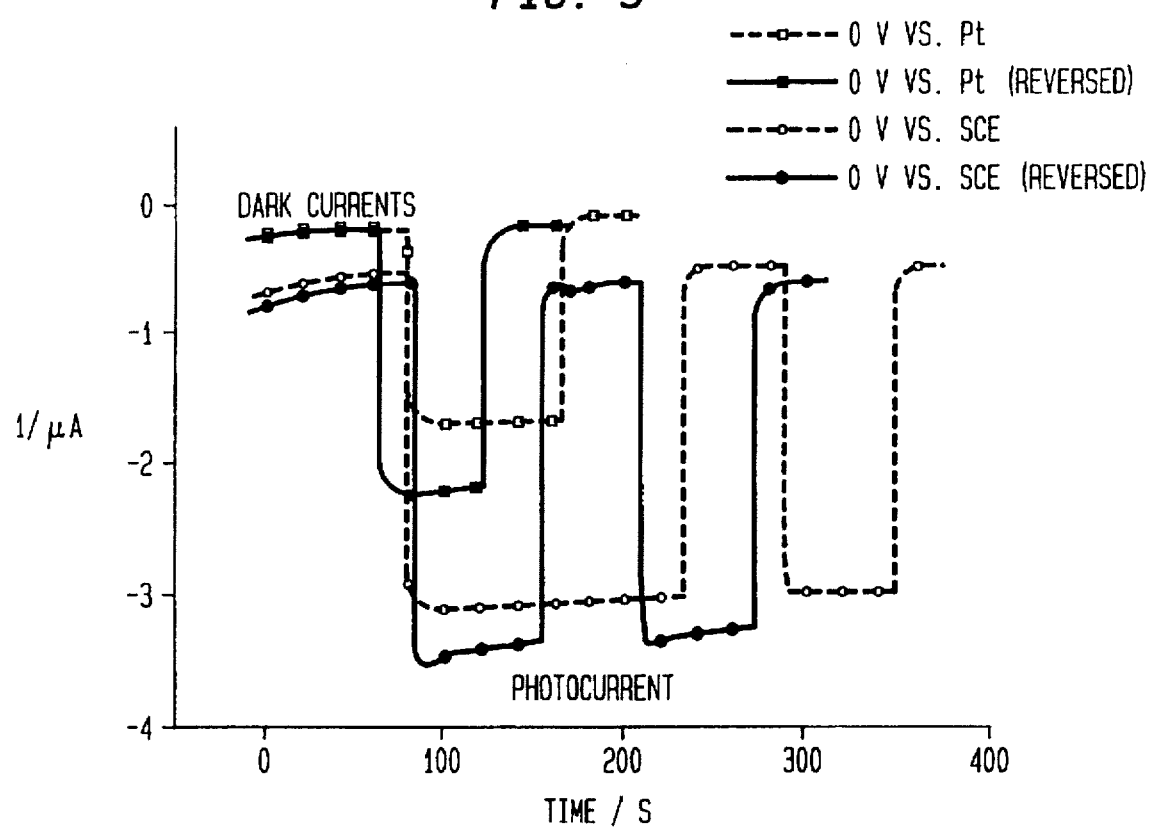
FIG. 9. is a graph of the photochemical measurements of films of Example 52.

The results of these tests are shown in the graph of FIG. 9.

EXAMPLE 53

Preparation of Au/4(PAPD)/4(PV) electrode:

A gold substrate was treated with thiophosphonic acid ($HS(CH_2)_4PO_3H_2$). The surface was then zirconated. (See e.g., W. R. Thompson, J. E. Pemberton, *Thin Sol-Gel Silica Films on (3-Mercaptopropyl)trimethoxysilane modified Ag and Au electrodes*, Chem. Mater. 7, 130–136 (1995)).

ZrPAPD/ZrPV fill was grown by alternate treatment in PAPD solution and in ZrOCl2 aqueous solution at room temperature (4 cycles of deposition), then by alternate treatment in PV solution and in ZrOCl2 aqueous solution at room temperature(next 4 cycles of deposition).

EXAMPLE 54

Photochemistry of Example 53
Current density versus time for the Au/4(PAPD)/4(PV) electrode.

The potential was set to 0.0 V versus SCE. Currents were obtained using a two electrode cell in a 0.1M NaClO$_4$ aqueous solution. The dark current is measured when no light is irradiating the sample. The current versus time was monitored with zero applied potential in the dark until the system stabilized, usually 3–4 min. The Au.PAPD/PV electrode was then exposed to light for approximately the same length of time and was then cycled back and forth between dark and light exposure.

Photocurrents were registered using a PAR potientiostat/Galvanostat Model 283 in a 0.1M NaClO$_4$ aqueous solution two electrode cell. The working electrode was the Au.PAPD/PV film-covered gold of Example 53 and the reference electrode (SCE) served also as the counter electrode. Measurements were also repeated using a three electrode cell and the results were identical, although the signal-to-noise ratio decreased.

Figure 10:
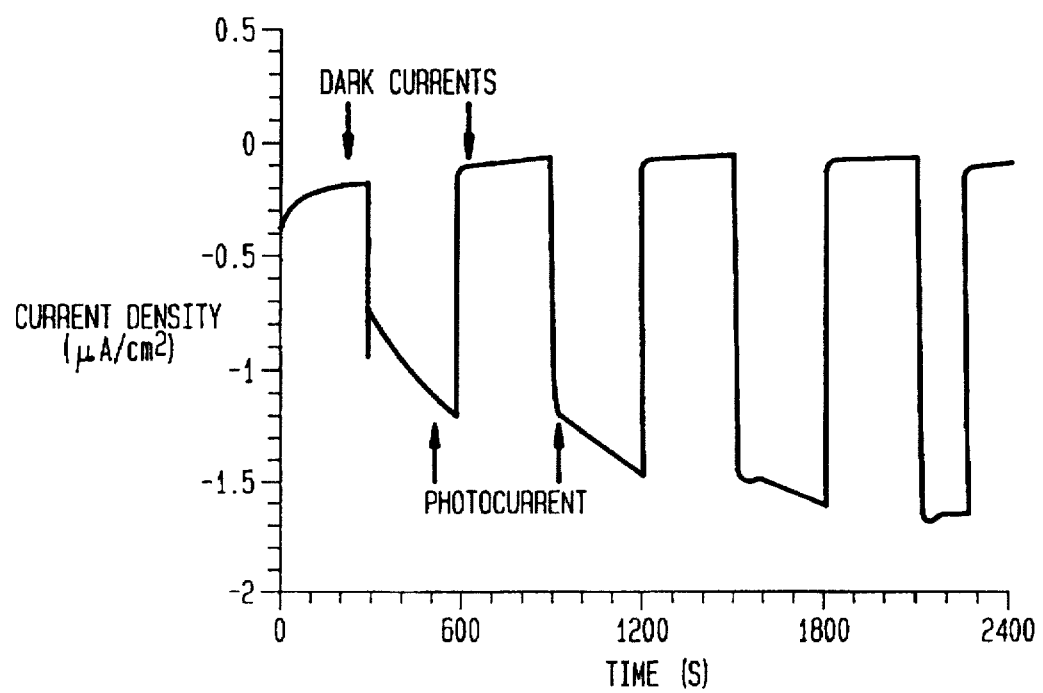
FIG. 10. is a graph of the photochemical measurements of films of Example 54.

Results are show in the graph of FIG. 10

EXAMPLE 55

Preparation of Au/4(PV)/4(PAPD) electrode:

A gold substrate was treated with thiophosphonic acid (HS(CH$_2$)$_4$PO$_3$H$_2$). The surface was then zirconated. (See e.g., W. R. Thompson, J. E. Pemberton, *Thin Sol-Gel Silica Films on (3-Mercaptopropyl)trimethoxysilane modified Ag and Au electrodes*, Chem. Mater. 7, 130–136 (1995)).

ZrPV/ZrPAPD was grown by alternate treatment in PV solution and in ZrOCl2 aqueous solution at room temperature (4 cycles of deposition), then by alternate treatment in PAPD solution and in ZrOCl2 aqueous solution at room temperature (next 4 cycles of deposition).

EXAMPLE 56

Photochemistry of Example 55
Current density versus time for the Au/4(PV)/4(PAPD) electrode.

The potential was set to 0.0 V versus SCE. Currents were obtained using a two electrode cell in a 0.1M EDTA aqueous solution under anaerobic conditions. The dark current is measured when no light is irradiating the sample. Photocurrents were obtained using an unfiltered 200 W Hg/Xe lamp. Positive current indicates the electrons flow to the gold electrode.

Figure 11:
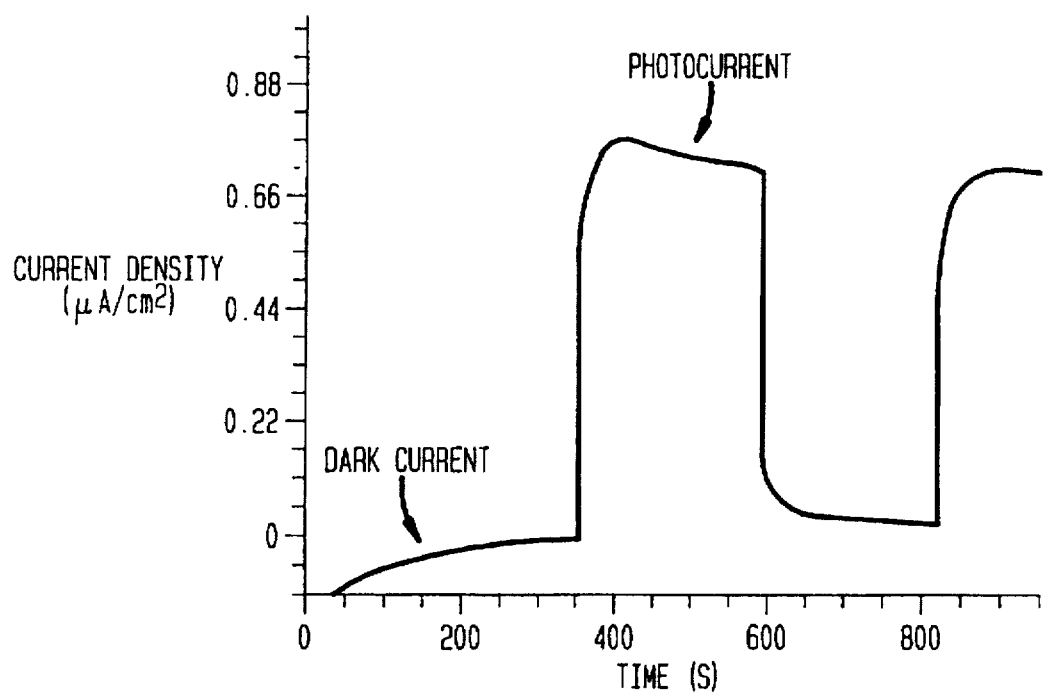
FIG. 11. is a graph of the photochemical measurements of films of Example 56.

Results are show in the graph of FIG. 11.

EXAMPLE 57

Preparation of Au/4(PAPD)/4(VBP) electrode:

A gold substrate was treated with thiophosphonic acid (HS(CH$_2$)$_4$PO$_3$H$_2$). The surface was then zirconated. (See e.g., W. R. Thompson, J. E. Pemberton, *Thin Sol-Gel Silica Films on (3-Mercaptopropyl)trimethoxysilane modified Ag and Au electrodes*, Chem. Mater. 7, 130–136 (1995)).

ZrPAPD/ZrVBP was grown by alternate treatment in PAPD solution and in ZrOCl2 aqueous solution at room temperature (4 cycles of deposition), then by alternate treatment in VBP solution and in ZrOCl2 aqueous solution at room temperature (next 4 cycles of deposition).

EXAMPLE 58

Photochemistry of Example 57
Current density versus time for the Au/4(PAPD)/4(VBP) electrode.

The potential was set to 0.0 V versus SCE. Currents were obtained using a two electrode cell in a 0.1M NaClO$_4$ aqueous solution. The dark current is measured when no light is irradiating the sample. Photocurrents were obtained using a 200 W Hg/Xe lamp with a UV filter (>330 nm). Negative current indicates the electrons flow from the gold electrode.

Figure 12:
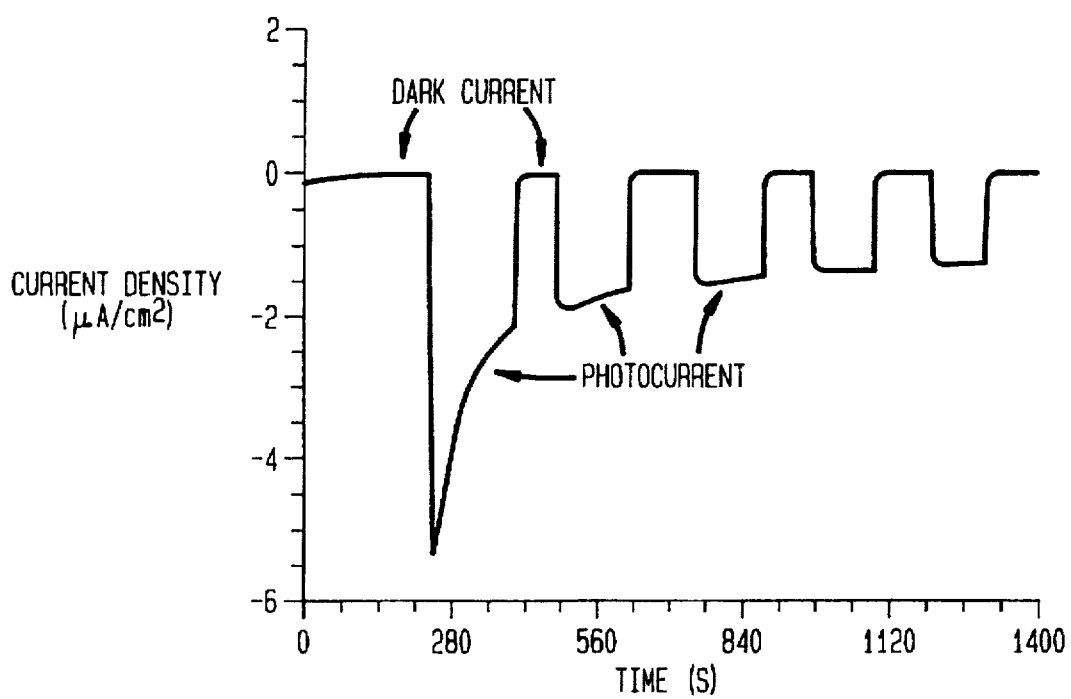
FIG. 12. is a graph of the photochemical measurements of films of Example 58.

Results are show in the graph of FIG. 12.

What is claimed is:

1. A photoelectrochemical device comprising a supporting substrate having on its surface a heterolamellar film comprising:

(i) a plurality of a complex of the formula:

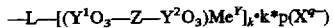

$$-L-[(Y^1O_3-Z-Y^2O_3)Me^y]_k \cdot k^* p(X^{q-})$$

wherein
   L is a linking means;
   each of $Y^1$ and $Y^2$, independently of the other, is phosphorus or arsenic;
   Z is a divalent group which reversibly forms a stable reduced form and stable oxidized form;
   X is an anion;
   $Me^y$ is $Me^1_n W_m$, where
      $Me^1$ is a divalent, trivalent, or tetravalent metal of Group III, IVA, or IVB having an atomic number of at least 21 or a lanthanide;
      W is an anion;
      n is 1, 2, or 3;
      m is 0, 1, 2, 3, or 4;
   k has a value of from 1 to about 250;
   p has a value of 0, 1, 2, or 3; and
   q is the charge on X,
   wherein each of $Y^1$, $Y^2$, Z, and $Me^1$ may be different for each successive k layer; wherein each of said complexes is bound to said substrate through the linking means, L.

2. The device of claim 1, wherein the film further comprises colloidal particles of at least one Group VIII metal at zero valence entrapped within said complexes by the $Me^1$ atoms.

3. A photoelectrochemical device comprising a supporting substrate having on its surface a film, said film comprising:

(i) two or more adjacent metal layers; said metal layers being disposed in substantially spaced, parallel relation to the substrate;

(ii) organic pillars covalently joined to two of said adjacent metal layers, forming a layer of pillars;

(iii) linking means binding said substrate to the metal layer closest to the substrate; wherein:

each metal layer, independently of the other, comprises:
   a) atoms of a trivalent or tetravalent metal of Group III, IVA, IVB having an atomic number of at least 21 or atoms of a lanthanide, forming a cohesive layer; and,
   b) anions bound to the metal atoms such that the metal ions have an effective valence of from $^{+1}$ to $^{+6}$;

said organic pillars are illustrated by the formula:

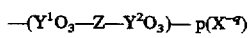

each of $Y^1$ and $Y^2$, independently of the other, is phosphorous or arsenic;

Z is capable of alternating between a stable reduced form and a stable oxidized form, wherein Z may be different for each layer of pillars;

X is an anion;

p has a value of 0, 1, 2 or 3; and, q is the charge on X.

4. A method for producing electrical energy comprising exposing a photoelectrochemical device to light, wherein said photoelectrochemical device comprises a supporting substrate having on its surface a heterolamellar film, said film comprising:

(i) a plurality of a complex of the formula:

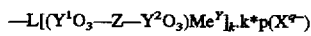

wherein

L is a linking means;

each of $Y^1$ and $Y^2$, independently of the other, is phosphorus or arsenic;

Z is a divalent group which reversibly forms a stable reduced form and stable oxidized form;

X is an anion;

$Me^Y$ is $Me^1_n W_m$, where $Me^1$ is a divalent, trivalent, or tetravalent metal of Group III, IVA, or IVB having an atomic number of at least 21 or a lanthanide;

W is an anion;

n is 1, 2, or 3;

m is 0, 1, 2, 3, or 4;

k has a value of from 1 to about 250;

p has a value of 0, 1, 2, or 3; and q is the charge on X, wherein each of $Y^1$, $Y^2$, Z, and $Me^1$ may be different for each successive k layer; wherein each of said complexes is bound to said substrate through the linking means, L.

* * * * *